US007361730B1

(12) United States Patent
Sauk

(10) Patent No.: US 7,361,730 B1
(45) Date of Patent: Apr. 22, 2008

(54) SURFACE LOCALIZED COLLIGIN/HSP47 IN CARCINOMA CELLS

(75) Inventor: John J. Sauk, Ellicot City, MD (US)

(73) Assignee: University of Maryland, Baltimore, MD (US)

( * ) Notice: Subject to any disclaimer, the term of this patent is extended or adjusted under 35 U.S.C. 154(b) by 0 days.

(21) Appl. No.: 09/936,565

(22) PCT Filed: Mar. 15, 2000

(86) PCT No.: PCT/US00/06588

§ 371 (c)(1),
(2), (4) Date: Feb. 4, 2002

(87) PCT Pub. No.: WO00/54805

PCT Pub. Date: Sep. 21, 2000

Related U.S. Application Data

(60) Provisional application No. 60/124,481, filed on Mar. 15, 1999.

(51) Int. Cl.
*C07K 5/00* (2006.01)
*A61K 38/00* (2006.01)

(52) U.S. Cl. .......................................... 530/300; 514/2
(58) Field of Classification Search ...................... None
See application file for complete search history.

(56) References Cited

U.S. PATENT DOCUMENTS

| 5,783,179 | A | * | 7/1998 | Nestor et al. | ............... | 424/85.2 |
| 5,932,478 | A | | 8/1999 | Multhoff | | |
| 5,962,424 | A | | 10/1999 | Hallahan et al. | | |
| 5,972,622 | A | * | 10/1999 | Desjardins | .................. | 435/7.1 |

FOREIGN PATENT DOCUMENTS

| WO | WO 95/03414 | * | 2/1995 |
| WO | WO 9729130 | | 8/1997 |

OTHER PUBLICATIONS

Orkin and Motulsky (NIH ad hoc Committee Dec. 1995—www.nih.gov/news/panelrep.html).*
Inder Verma (Nature 1997; 389:239-242).*
Friedmann ( Scientific American Jun. 1997; pp. 96-101.*
Rubanyi (Mol. Aspects of Med. 2001;22:113-142.*
Ross et al (Human Gene Therapy 1996;7: 1781-1790).*
Homma MK et al (Cell Growth and Differentiation Mar. 1996;7(3):281-288).*
Peptides: Chem. Biochem., Proc. Amer. Peptide Symp., 1st (1970), meeting date 1968, 99-112.*
Vankann et al (J. Colloid and Interface Science 1996;178(1):241-250).*
Larocca et al., "Gene transfer to mammalian cells using genetically targeted filamentous bacteriophage," The FASEB Journal, vol. 13, Apr. 1999, pp. 727-734.

Database Medline on Dialog, US National Library of Medicine, (Bethesda, MD, USA), No. 1999436824 Razzaque et al., "The possible role of colligin/hsp 47, a collagen binding protein in the pathogenesis of human and experimental fibrotic diseases," Histology and Histopathology Oct. 1999, vol. 14, No. 4, pp. 1199-1212.
Database Medline on Dialog, US National Library of Medicine, (Bethesda, MD, USA), No. 1999241927 Norris et al "Cell Surface Colligin/Hsp47 associates with tetraspanin protein CD9 in epidermoid carcinoma cell lines," Journal of cellular Biochemistry, May 1999, vol. 73, No. 2, pp. 248-258.
Geng Hu et al., "Endoplasmic Reticulum Protein Hsp47 Binds Specifically to the N-Terminal Globular Domain of the Amino-Propeptide of the Procollagen 1 a1 (l)-Chain," Journal of Cellular Biochemistry, vol. 59, pp. 350-367 1995.
Timothy Smith et al., "Hsp47 And Cyclophilin B Traverse the Endoplasmic Reticulum with Procollagen into Pre-Golgi Intermediate Vesicles," The Journal of Biological Chemistry, vol. 270, No. 31, Issue of Aug. 4, 1995, pp. 18323-18328.
Luciano R. Ferreira et al., "Hsp47 And Other ER-Resident Molecular Chaperones Form Heterocomplexes With Each Other and With Collagen Type IV Chains," Connective Tissue Research 1996, vol. 33, No. 4, pp. 265-273.
Hessam Siavash et al., "Inhibition of Cysteine Proteinases by Autolytic Digestion is Mediated by CBP2/Hsp47," Connective Tissue Research, vol. 43, pp. 1-6, 2002.
Carla Herbert et al., "Cell Surface Colligin/Hsp47 Associates With Tetraspanin Protein CD9 in Epidermoid Carcinoma Cell Lines," Journal of Cellular Biochemistry, vol. 73, pp. 248-258, 1999.
Ricardo Della Coletta et al., "Increase in Expression of Hsp47 And Collagen in Hereditary Gingival Fibromatosis is Modulated by Stress And Terminal Procollagen N-Propeptides," Connective Tissue Research, vol. 40(4), pp. 237-249, 1999.
Carla Herbert et al., Non-Natural CBP2 Binding Peptides and Peptomers Modulate Carcinoma Cell Adhesion and Invasion, Journal of Cellular Biochemistry vol. 82, pp. 145-154, 2001.
John J Sauk et al "Binding Motifs of CBP2 A Potential Cell Surface Target for Carcinoma Cells" Journal of Cellular Biochemistry, vol. 78, pp. 261-263. 2000.
Search Results on HSP47.
Abstract of Koide et al. J Biol Chem Feb. 22, 2002 277(8) 6178-82.
Patents Abstracts of Japan, Abstract of JP 07072156, Mar. 17, 1995.
Hu Geng et al., "Endoplasmic reticulum protein Hsp47 binds specifically to the N-terminal globular domain of the amino-propeptide of the procollagen I alpha-1(I)-chain," Journal of Cellular Biochemistry, 1995, pp. 350-367, vol. 59, No. 3.

(Continued)

*Primary Examiner*—Christopher Yaen
(74) *Attorney, Agent, or Firm*—Millen, White, Zelano, Branigan, P.C.

(57) ABSTRACT

This invention relates, e.g., to colligin/Hsp47 molecules which are expressed on the surface of carcinoma cells and to the use of such expressed molecules as targets for, e.g., therapeutic agents or imaging agents. The invention also relates to peptides which bind specifically to external domains of such surface-localized Hsp47 molecules.

15 Claims, No Drawings

OTHER PUBLICATIONS

Hebert Carla et al., "Cell surface colligin/Hsp47 associates with tetraspanin protein CD9 in epidermoid carcinoma cell lines," Journal of Cellular Biochemistry, May 1, 1999, pp. 248-258, vol. 73, No. 2.

Morino Masayoshi et al., "HSP47 as a possible marker for malignancy of tumors in vivo," In Vivo, 1994, pp. 285-288, vol. 8, No. 3.

Morino Masayoshi et al., "Marked induction of HSP47, a collagen-binding stress protein, during solid tumor formation of ascitic Sarcoma 180 in vivo," In Vivo, 1995, pp. 503-507, vol. 9, No. 5.

Morino Masayoshi et al., "Specific expression of HSP47 in human tumor cell lines in vitro," In Vivo, 1997, pp. 17-22, vol. 11, No. 1.

John J. Sauk et al., "Binding motifs of CBP2 a potential cell surface target for carcinoma cells," Journal of Cellular Biochemistry, May 2000, pp. 251-263, vol. 78, No. 2.

Hebert Carla et al., "Non-natural CBP2 binding peptides and peptomers modulate carcinoma cell adhesion and invasion," Journal of Cellular Biochemistry, 2001, pp. 145-154, vol. 82, No. 1.

* cited by examiner

SURFACE LOCALIZED COLLIGIN/HSP47 IN CARCINOMA CELLS

This application claims the benefit of U.S. Provisional Application 60/124,481, filed Mar. 15, 1999, which is incorporated by reference herein in its entirety.

DESCRIPTION OF THE INVENTION

This invention relates, e.g., to colligin/Hsp47 molecules which are expressed on the surface of carcinoma cells and to the use of such expressed molecules as targets for, e.g., therapeutic agents or imaging agents. The invention also relates to peptides which bind specifically to external domains of such surface-localized Hsp47 molecules.

The heat shock protein colligin/CBP2/Hsp47 (sometimes referred to herein as Hsp47) can act as a molecular chaperone for collagen. In normal cells, Hsp47 becomes closely associated with nascent chains of procollagen early during its translation and accompanies the protein from the endoplasmic reticulum (ER) to the Golgi, whereupon collagen dissociates and is secreted, and the chaperone is recycled back to the ER. It is disclosed herein that, surprisingly, in carcinoma cells Hsp47 is not efficiently recycled to the ER but, rather, is localized on (e.g., leaks onto) the surface of the cells.

Examples 1 and 6 show that Hsp47 is localized on the surface of a number of carcinoma cell lines, including human oral squamous cell carcinoma lines, a murine epidermal cell line, breast cancer carcinoma lines and prostate cancer cell lines, but is not expressed on the surface of control, non-carcinoma cells. Thus, cell-surface localized Hsp47 can serve as a marker and/or "homing target" for carcinoma cells. Example 2 shows that at least of portion of surface localized Hsp47 is available for binding to, e.g., a procollagen propeptide to which it normally binds in the intracellular environment. By targeting carcinoma cells with an agent that interacts specifically with available portions of Hsp47 expressed on the surface of the cells, one can deliver therapeutic agents efficiently, allowing for reduced doses required to achieve therapeutic effects and reduced side effects; and one can sensitively detect or image carcinoma cells, or carcinomas or tumors containing them, above a background of non-carcinoma cells.

This invention relates to a method for modulating a cell which expresses Hsp47 on its surface, comprising administering to the cell an effective amount of an agent which binds to an (at least one) external domain of Hsp47. The invention also relates to a method for treating a patient suffering from a carcinoma in which Hsp47 is expressed on the surface of at least some of the carcinoma cells, comprising administering to the patient an effective amount of an agent which binds specifically to an external domain of Hsp47. In a preferred embodiment, the agent comprises a targeting moiety which is specific for Hsp47, and a therapeutic moiety, e.g., a drug or toxic substance. In one embodiment, the targeting moiety comprises an antibody, or a fragment or variant thereof, which is specific for an external domain of Hsp47. In another embodiment, the targeting moiety comprises a peptide which is specific for an external domain of Hsp47, e.g., a peptide having the consensus motif XHyHyXXHyXXXXHyHy (SEQ ID NO: 1) or the consensus motif HyXXXHyHyXXHyXXX (SEQ ID NO: 2). In a most preferred embodiment, the peptide has the sequence of one of SEQ ID NOs: 3-25. In yet another embodiment, the targeting moiety comprises a bacteriophage on whose surface is a peptide such as those disclosed above.

The invention also relates to a diagnostic imaging method of detecting a cell which expresses Hsp47 on its surface (e.g., a carcinoma cell, or a carcinoma or tumor comprising such a cell), comprising contacting the cell with an agent comprising a targeting moiety that binds specifically to an external domain of Hsp47, and a detectable label (detectable moiety) (e.g., a label which is detectable by MRI, X-Ray, gamma scintigraphy, CT scanning, or the like). The targeting moiety can comprise, e.g., an antibody, a peptide or a bacteriophage as described above.

The invention also relates to a method of screening for an agent which binds specifically to a carcinoma in which Hsp47 is expressed on the surface of at least some of the carcinoma cells, comprising identifying an agent which binds specifically to an external domain of Hsp47. In a preferred embodiment, the agent is useful for treating a carcinoma in a patient or for diagnosing a carcinoma in a patient.

The invention also relates to kits for detecting a carcinoma cell or for treating a carcinoma cell, comprising a targeting moiety which binds specifically to an external domain of Hsp47

The invention also relates to peptides which bind specifically to an external domain of Hsp47. In a preferred embodiment, the peptide contains the consensus motif XHyHyXXHyXXXXHyHy (SEQ ID NO: 1) or the consensus motif HyXXXHyHyXXHyXXX (SEQ ID NO: 2). In a most preferred embodiment, the peptide is one of SEQ ID NOs: 3-25.

Any type of cell which expresses Hsp47 on its surface can be modulated, treated and/or detected by the methods of the invention. In a preferred embodiment, the cell is a carcinoma cell. The term "carcinoma" as used herein means any of the various types of malignant neoplasms derived from epithelial tissue in any of several sites, e.g., skin, basal cells, large intestine, lung, colon, breast, bladder, oral, head and neck, larynx, nasopharynx, adrenal cortex, apocrine gland, cloaca, embryonal cells, kidney, liver, pancreas, or prostate. The term "carcinoma cell" as used herein applies to a carcinoma cell, in vivo or in vitro, whether it occurs as an individual cell or in the context of a tissue, carcinoma in any stage of development, a tumor, a metastasis (including a micrometastasis), or the like.

Sarcoma cells are also encompassed by the invention. The term "sarcoma" as used herein means any connective tissue neoplasm, formed by the proliferation of mesodermal cells. Among the many types of sarcomas encompassed by the invention are fibrosarcomsa, rhabdosarcoma, neurofibrosarcoma and osteosarcoma. The term "sarcoma cell" as used herein applies to a sarcoma cell, in vivo or in vitro, whether it occurs as an individual cell or in the context of a tissue, a sarcoma in any stage of development, a tumor, a metastasis (including a micrometastasis), or the like. Methods to study sarcoma cells, particularly in relation to the expression of Hsp47, are disclosed, e.g., in Morino et al. (1997). *In Vivo* 11, 261-4; Morino et al. (1997). *In Vivo* 11, 17-21; Shirakami et al (1995). *In Vivo* 9, 513-8; Shirakami et al (1995). *In Vivo* 9, 509-12; Morino et al. (1995). *In Vivo* 9, 503-8; and Morino et al. (1994). *In Vivo* 8, 285-8.

Methods and reagents such as those discussed herein in relation to carcinoma cells are, of course, applicable to any type of cell having surface expression of Hsp47, and to any physiological or pathological condition associated with such expression.

Hsp47 has been cloned and/or sequenced from a number of organisms, including, e.g., chicken (Hiroyashi et al. (1991). *Mol. and Cell Biol.* 11, 4036-4044); mouse (Takechi et al. (1992). *Eur. J. of Biochem* 206, 323-329); and human (e.g., Nakamura, accession number #D83174 in the DDJB/EMBL/GenBank databases; Ikegawa et al. (1995). *Cytogenet. Cell Genet.* 71, 182-186); and Jain et al. (1994). *Arch. Biochem. & Biophys.* 314, 23-30).

The term "Hsp47," as used herein, encompasses, e.g., wild type Hsp47 from any mammalian source, preferably human, or a variant thereof. By "variant" of Hsp47 is meant, e.g., any insertion, deletion, mutant form or substitution, either conservative or non-conservative, in either an internal or external domain of the protein, wherein such changes do not substantially alter the binding of the external domain to a targeting moiety as defined herein. By "conservative substitutions" is meant by combinations such as Gly. Ala; Val, Ile, Leu; Asp, Glu; Asn, Gln; Ser, Thr; Lys, Arg; and Phe, Tyr. Variants can include, e.g., homologs, analogs, muteins and mimetics (mimotopes). Many types of protein modifications, including post-translational modifications, are included. See, e.g., modifications disclosed in U.S. Pat. No. 5,935,835. Hsp47 molecules which are modified so that they possess properties not normally associated with wild type Hsp47 are included, provided that an external domain can bind specifically to a targeting moiety of the invention.

An agent which binds to Hsp47 expressed (e.g., localized, located) on the surface of a cell can bind to one or more of any portion(s) or fragment(s) of the Hsp47 molecule, of any length, which are available for binding. Such an available sequence is referred to herein as an "external domain" of the Hsp47 protein.

An agent or moiety which "binds specifically" to ("is specific for"; binds "preferentially" to) an external domain of Hsp47 interacts with it, or forms or undergoes a physical association with it, in an amount and for a sufficient time to allow detection of the cell, or to modulate it (e.g., to elicit a therapeutic response). By "specifically" or "preferentially" is meant that the agent has a higher affinity, e.g., a higher degree of selectivity, for an external domain of Hsp47 than for other molecules located on the surface of a cell. Similarly, an agent or moiety which binds specifically to a particular type of cell, e.g. a carcinoma cell, has a higher affinity, e.g., a higher degree of selectivity, for that type of cell than for a normal (e.g., non-carcinoma) cell, such that the binding allows the carcinoma cell to be detected and distinguished from a background of normal cells, and/or allows for contacting a therapeutic moiety with a carcinoma cell but not (to a significant degree) with neighboring non-carconoma cells. The affinity or degree of specificity can be determined by any of a variety of routine procedures. e.g., competitive binding studies. See, e.g., Czerwinski et al. (1998) *Proc. Nat. Acad. Sci.* 95, 11, 520-11, 525 and Moe et al. (1998). *Phar. Res*, 23, 31-38. The portion of an agent which binds specifically to an external domain of Hsp47 can be referred to as a "targeting moiety," a "site-directed macromolecule," a "ligand" or an "affinity ligand."

Any agent or moiety which binds specifically to an external domain of Hsp47 is encompassed by the invention.

One type of targeting moiety comprises an antibody which binds specifically to an external domain of Hsp47. The term "antibody" as used herein can mean a polyclonal or, preferably, a monoclonal antibody, or a fragment (of any size) of a polyclonal or monoclonal antibody, e.g., Fv, Fab', Fab, F(ab')$_2$, Fab'Fc, or the like. Single chain antibodies are also encompassed by the invention. Any form of immunoglobulin is included, e.g., immunoglobulins A,D,E,G or M. One may wish to employ an intact antibody (e.g., an IgG molecule), a bi- or multi-valent antibody which has specificity for at least two antigens, or a univalent antibody fragment. Antibodies of the invention can be isolated from natural sources; from hybridomas lymphomas, or the like; or they can be produced by synthetic and/or recombinant means. They can be partially or completely humanized, using conventional. art-recognized procedures, as described, e.g., in Jones et al. (1986). *Nature* 321, 522; Riechmann et al. (1988). *Nature* 332, 323; Verhoyen et al. (1988). *Science* 239, 1534; Carter et al. (1992). *Proc. Natl. Acad. Sci. USA* 89, 4285; Sandhu (1992). *Crit. Rev. Biotech.* 12, 437; and Singer et al. (1933). *J. Immunol.* 150, 2844.

Methods to screen for, isolate, purify, manipulate, etc. antibodies which exhibit the requisite specificity and/or affinity are conventional and routine in the art and are disclosed in, e.g., U.S. Pat. No. 4,196,265; Roitt I., (1994). *Essential Immunology*, Blackwell Scientific Publications, London; Coligan et al., *Current Protocols in Immunology*; Barnes et al., in *Methods in Molecular Biology, Vol.* 10, pages 79-104 (Humana Press 1992); Harlow et al., *Antibodies: A Laboratory Manual*, page 726 (Cold Spring Harbor Pub. 1988); and *Current Protocols in Immunology*; Edited by John E. Coligan et al., John Wiley & Sons, Inc.

Another type of targeting moiety comprises a peptide which binds specifically to an external domain of Hsp47. Such a peptide can be of any size or amino acid composition effective to bind specifically to an external domain of Hsp47, so as to allows the formation of a detectable entity or the production of a therapeutic response. In a preferred embodiment, the peptide is not full length collagen, and is not naturally occurring collagen or a fragment thereof. In a preferred embodiment, the peptide is less than about 90 amino acids, e.g., about 80, 70, 60, 50, 40, 30, 20 or 10 amino acids, most preferably about 12-16 amino acids. The invention also encompasses larger polypeptides, which can be, e.g., as long as a full-length procollagen, providing that the polypeptide can bind to an external domain of Hsp47, so as to allow the formation of a detectable entity or the production of a therapeutic response.

Methods to determine if a peptide (or any other agent of interest) binds to a surface-expressed Hsp47 molecule are conventional and routine in the art. See, e.g., Takemoto et al. (1992). *Arch. Biochem. and Biophys.* 296, 323-329; Altemeyer et al. (1996). *International J. of Cancer* 69, 340-349; Ferrarini et al. (1992). *International J. of Cancer* 51, 613-619; Ullrich et al. (1986). *Proc. Natl. Acad. Sci.* 83, 3121-3125; Vanburskirk et al. (1989). *J. Exp. Med.* 170, 1799-1809; Freedman et al. (1992). *J. of Neuroimmunology* 41, 231-238; Sauk et al. (1997). *Connect. Tissue Res.* 37, 105-119); and U.S. Pat. No. 5,932,478. Such methods include, e.g., detection of an agent which is tagged, directly or indirectly, with a fluorescent label by immunofluorescence microscopy, including confocal microscopy, or by flow cytometry (FACscan); detection of a radioactively labeled agent by autoradiography; electron microscopy; immunostaining; subcellular fractionation; or the like. Examples 1 and 6 illustrate some typical methods.

A number of peptides or peptide sequences have been identified which interact with intracellular Hsp47, and/or with the isolated protein. These peptides include, e.g., the region of procollagen defined by the anti-propeptide antibody SP1.D8 (Hu et al. (1995). *J. of Cellular Biochemistry* 59, 350-367); the N-propeptide region of procollagen of the α1(I)-chain between residues 23-151, in particular residues 23-108; Gly-Xaa-Yaa sequences of procollagen, where X and Y are, independently, any amino acid; the (Pro-Pro-Gly)$_n$ model sequences of collagen; and portions of gelatin (Nagata et al. (1988). *Biochem. Biophys. Res. Comm.* 153, 428-434). Such peptides, or variants, mimetics (mimotopes), muteins, analogs or fragments thereof, can be tested readily for their ability to interact specifically with an external domain of Hsp47; and those which bind avidly and/or selectively can be used as targeting moieties in the invention.

By "variants" is meant any insertion, deletion, mutant form or substitution, either conservative or non-conservative, where such changes do not substantially alter the binding of the peptide to an external domain of Hsp47. Types of variants include those discussed herein with reference to Hsp47 molecules. Among the modified peptides which are encompassed by the invention are peptidomimetics, which can be generated and tested by routine, conventional means. See, e.g., al-Obeidi et al. (1998). *Mol Biotechnol.* 9, 205-23; Kieber-Emmons et al. (1997). *Curr. Opin. Biotechnol.* 8, 435-41; Bowditch et al. (1996) *Blood* 88, 4579-4584; and Partidos et al. (1997) *Immunology Letters* 57, 113-116.

Methods to measure such binding constants/determine avidity are conventional in the art. See, e.g., Blond-Elguindi et al. (1993) *Cell* 75, 717-728. In a preferred embodiment, the binding constant (avidity) of the peptide or peptide region with Hsp47 is 15-45 µm; most preferably, the binding constant is 20-30 µm.

A technique for identifying peptides that can bind specifically and/or avidly to surface-expressed Hsp47 (external domains) is bacteriophage display (phage display) combined with affinity panning. See, e.g., Smith et al. (1993). *Methods Enzymol.* 217, 228-57; Smith et al. (1995). *J. Biol. Chem.* 270, 18, 323-328; Kitamura et al. (1992). *Cell* 69, 823-831; Burkhardt et al. (1991). *Proc. Natl. Acad. Sci.* 88, 7410-7414; Pasqualini et al. (1996). *Brazilian J. of Med. & Biol. Res.* 29, 1151-1158; Pasqualini et al. (1996). *Molecular Psychiatry* 1, 423; Ruoslahti (1996). *Ann. Rev. of Cell & Developmental Biology* 12, 697-715; Ruoslahti (1997). Kidney International 51, 1413-1417; Hutchcroft et al. (1992). *J. Biol. Chem.* 267, 8613-8619; and Borst et al. (1993). *Immunological Reviews* 132, 49-84. Among the types of phage which can be used are single stranded filamentous phage, e.g., fd, F2, F5, M13, and variants thereof. Briefly, a set of random peptides of a chosen length (e.g., 7-mers or 12-mers) are cloned into and displayed on the surface of bacteriophage, and phage are selected which bind preferentially to cells bearing surface-expressed Hsp47, following one or more cycles of selection.

A demonstration of such panning is shown in Example 5. Phage-displayed 12-mer peptides identified in this Example contain, in general, either the consensus motif, XHyHyXX-HyXXXXHyHy (SEQ ID NO: 1) or the consensus motif HyXXXHyHyXXHyXXX (SEQ ID NO: 2), where X is independently any amino acid and Hy is independently any hydrophobic amino acid. In a preferred embodiment, the hydrophobic amino acid is a large one, e.g., W (Trp), L(Leu) or F(Phe). Among the peptides having the consensus motif SEQ ID NO: 1 are those having the sequence of SEQ ID NO:3 to SEQ ID NO: 13, as shown in Table 1. These peptides can be characterized as predominantly hydrophobic peptides.

TABLE 1

| PREDOMINANTLY HYDROPHOBIC PEPTIDES | |
|---|---|
| WHWQWTPWSIQP | (SEQ. ID NO. 3) |
| WHYPWFQNWAMA | (SEQ. ID NO. 4) |
| WHWNGWKYPVVD | (SEQ. ID NO. 5) |
| FHWPTLYNMYIP | (SEQ. ID NO. 6) |

TABLE 1-continued

| PREDOMINANTLY HYDROPHOBIC PEPTIDES | |
|---|---|
| FHWSWYTPSRPS | (SEQ. ID NO. 7) |
| WHWSYPLWGPLE | (SEQ. ID NO. 8) |
| NWTLPTAQFAYL | (SEQ. ID NO. 9) |
| VLIPVKALRAVW | (SEQ. ID NO. 10) |
| TPQPNMMLRISP | (SEQ. ID NO. II) |
| ANFTFFKLMPVS | (SEQ. ID NO. 12) |
| KVPPALPSPWTS | (SEQ. ID NO. 13) |

Among the peptides having the consensus motif SEQ ID NO: 2 are those having the sequence of SEQ ID NO: 14 to SEQ ID NO: 25, as shown in Table 2. These peptides can be characterized as predominantly hydrophobic peptides.

TABLE 2

| PREDOMINANTLY HYDROPIHLIC PEPTIDES | |
|---|---|
| GLYMHPPTHTMR | (SEQ. ID NO. 14) |
| EGRSTLTSLTII | (SEQ. ID NO. 15) |
| SGAANQPSATSG | (SEQ. ID NO. 16) |
| KHNEQTFHPKVP | (SEQ. ID NO. 17) |
| TVLHSLAHQTFI | (SEQ. ID NO. 18) |
| AQSMDVYSRQPF | (SEQ. ID NO. 19) |
| NTPTAPWHPGES | (SEQ. iD NO. 20) |
| RYMNDHKSPTDS | (SEQ. ID NO. 21) |
| SNAQEDVHDLSS | (SEQ. ID NO. 22) |
| TPSPNKSTVSPG | (SEQ. ID NO. 23) |
| KFMQAQAGMTHN | (SEQ. ID NO. 24) |
| LDSRYSLQAAMY | (SEQ. ID NO. 25) |

The predominantly hydrophobic peptides identified in Example 5 surprisingly do not exhibit specific sequence identity to regions of procollagen, which is known to bind to Hsp47 but, taking into account the hydropathic profile of the amino acids (see discussion in Example 5), nevertheless map primarily to regions within the N-propeptide region of collagen (residues 59-71) or the C-propeptide region (residues 1344-1445). The predominantly hydrophilic peptides also do not exhibit specific sequence identity to regions of procollagen, but generally map to regions within the helical region of procollagen.

Among the phage-displayed 7-mer peptides identified in Example 5 are those having the sequence of SEQ ID NO:26 to SEQ ID NO: 62, as shown in Table 3.

TABLE 3

| 7-MER PEPTIDES | |
|---|---|
| GITSLLS | (SEQ. ID NO. 26) |
| FHSGWPQ | (SEQ. ID NO. 27) |
| TTNYYTN | (SEQ. ID NO. 28) |
| EPAHRSY | (SEQ. ID NO. 29) |
| SNAATEY | (SEQ. ID NO. 30) |
| KLSMTIP | (SEQ. ID NO. 31) |
| LVNMPTP | (SEQ. ID NO. 32) |
| SPNPWYG | (SEQ. ID NO. 33) |
| SLSTTQK | (SEQ. ID NO. 34) |
| TDTPRRQ | (SEQ. ID NO. 35) |
| KLTNTVL | (SEQ. ID NO. 36) |
| NWVPRTN | (SEQ. ID NO. 37) |
| TATSLQW | (SEQ. ID NO. 38) |
| KLPNVNS | (SEQ. ID NO. 39) |
| NVPYVVH | (SEQ. ID NO. 40) |
| DRFSPMP | (SEQ. ID NO. 41) |
| HFQPRHH | (SEQ. ID NO. 42) |
| HSTSTPH | (SEQ. ID NO. 43) |
| YVASPWQ | (SEQ. ID NO. 44) |
| FRYDTFP | (SEQ. ID NO. 45) |

TABLE 3-continued

7-MER PEPTIDES

| | |
|---|---|
| HNYLNLT | (SEQ. ID NO. 46) |
| ISQGTTP | (SEQ. ID NO. 47) |
| EFLPVQL | (SEQ. ID NO. 48) |
| HNYLNLT | (SEQ. ID NO. 49) |
| HPSLNKP | (SEQ. ID NO. 50) |
| HSTSVTQ | (SEQ. ID NO. 51) |
| YVASWPO | (SEQ. ID NO. 52) |
| ITVQKNT | (SEQ. ID NO. 53) |
| VAGNPLQ | (SEQ. ID NO. 54) |
| FTIPSNL | (SEQ. ID NO. 55) |
| NVMIKGQ | (SEQ. ID NO. 56) |
| QKPPPYD | (SEQ. ID NO. 57) |
| NVPYGVH | (SEQ. ID NO. 58) |
| AFLPSKL | (SEQ. ID NO. 59) |
| HFQPRHH | (SEQ. ID NO. 60) |
| NTSPLEL | (SEQ. ID NO. 61) |
| DFNYNPL | (SEQ. ID NO. 62) |

Peptides according to the invention include the SEQ IDs disclosed herein, as well as peptides which are extended by as many as, e.g., 20 additional amino acids (e.g., about 1, 3, 6, 9, 12, 15 or 18) on either or both ends of the peptide, provided that the extended peptide exhibits the requisite specificity/avidity for an external domain of Hsp47.

Preferably, a peptide of the invention is "isolated," e.g., is in a form other than it occurs in nature, e.g., in a buffer, in a dry form awaiting reconstitution, as part of a kit, etc. In some embodiments, the peptide is substantially purified. The term "substantially purified", as used herein, refers to a molecule, such as a peptide, that is substantially free of other proteins, lipids, carbohydrates, nucleic acids, and other biological materials with which it is naturally associated. For example, a substantially pure molecule, such as a peptide, can be at least about 60%, by dry weight, preferably about 70%, 80%, 90%, 95% or 99% the molecule of interest. One skilled in the art can purify peptides using standard protein purification methods and the purity of the peptides can be determined using standard methods including, e.g., polyacrylamide gel electrophoresis (e.g., SDS-PAGE), column chromatography (e.g., high performance liquid chromatography (HPLC), and amino-terminal amino acid sequence analysis.

Once peptides exhibiting a specificity for surface-expressed Hsp47 are identified, free energy calculations or other properties can be determined for each, and this information can be used to design other agents or drugs, e.g., organic compounds, which bind preferentially to surface expressed Hsp47. Such methods are conventional. See, e.g., Rejyo et al. (1996) *Proc. Natl. Acad. Sci.* 93, 8945-8950; Gabius et al. (1998) *Phar. Res.* 15, 23-30; and Selz et al. (1998) *Biophysical Jol.* 75, 2332-2343.

Phage display/panning techniques can not only serve to identify peptides which can be used in the invention, but can also provide bacteriophage bearing such peptides on their surface which can be used in the invention. That is, a targeting moiety of the invention can be the peptide-bearing bacteriophage, itself. Such bacteriophage exhibit the advantage that they are readily internalized into the ER of cells to which they adhere. See, e.g., Example 6.

In one aspect of the invention, a targeting moiety as above is used to deliver a therapeutic moiety (e.g., a drug or toxic substance) to a cell which expresses Hsp47 on it surface (e.g., a carcinoma cell, for example one which constitutes part of a tissue or a tumor). A therapeutic agent of the invention preferably comprises a targeting moiety and, associated with it, a therapeutic moiety. A therapeutic agent can modulate a cell either positively or negatively, providing that it has a net therapeutic effect on the environment in which the cell resides (e.g., a tissue, tumor, metastasis, patient, or the like). By "modulate" is meant that any physiological response of the cell, e.g., a metabolic activity, a response to an internal or external environmental factor, a synthetic or catabolic process, activation, repression, etc., is altered. The therapeutic agent can achieve inhibition or suppression of growth, killing, destruction, elimination, control, modification, etc. of the cell or tissue. Cytostatic, cytolytic, cytotoxic, and carcinostatic effects are included. A therapeutic agent can suppress a neoplastic phenotype, or it can interfere with normal function of, or otherwise incapacitate, a cell to which it is delivered. In one embodiment, the therapeutic agent can prevent the establishment, growth or metastasis of a carcinoma, e.g., can prevent the reoccurrence of a carcinoma. Representative examples of antitumor agents, such as, e.g., immune activators and tumor proliferation inhibitors, are disclosed, e.g., in U.S. Pat. No. 5,662,896. "treatment" of, or the elicitation of a "therapeutic response" in, a cell, tissue, tumor, metastasis, patient, or the like, by a therapeutic agent (e.g., comprising a drug or toxic agent) is defined herein as an action which can bring about a response such as those discussed above. By an "effective amount" of a therapeutic agent is meant an amount which is sufficient to bring about such a response.

Methods to assay whether an agent elicits a therapeutic effect are routine and conventional, and can be performed in vitro or in vivo. A typical method for performing pharmacokinetics in an animal model is shown in Example 7. A typical animal model for testing the effect of an agent on tumors is the human oral squamous cell carcinoma xenograft model, is shown in Example 7. Among the factors which can be assayed are survival rate of the animal, reduction in size of a treated tumor, and the presence or absence of metastases, such as lymph node or lung metastasis.

Any of a wide variety of therapeutic moieties is encompassed by the invention, including therapeutic compounds which are used currently, but are delivered to cells by other methods. The therapeutic moieties can be isolated from natural sources, or can be produced by synthetic and/or recombinant means, all of which are well-known to one of ordinary skill in the art. Among the drugs or therapeutic moieties which can be used in the invention are chemotherapeutic and/or cytotoxic agents such as, e.g., steroids, antimetabolites, anthracycline, vincaalkaloids, neocarzinostatin (NCS), adriamycin, dideoxycytidine, cisplatin, doxorubicin, pirarubicin, melphalan and daunomycin, or the like. Methods to attach such moieties to targeting moieties are routine and conventional. For example, Example 7 illustrates methods to attach doxorubicin to an antibody or peptide targeting agent.

In one embodiment, the therapeutic moiety comprises a toxin such as, e.g., ricin (e.g., the A and/or B chain thereof, or the deglycosylated form), poisonous lectins, diphtheria toxin, exotoxin from *Psuedomonas aeruginosa*, abrin, modeccin, botulina toxin, alpha-amanitan, pokeweed antiviral protein (PAP, including PAPI, PAPII and PAP-S), ribosome inhibiting proteins, especially the ribosome inhibiting proteins of barley, wheat, corn, rye, or gelonin, or ribosome-inactivating glycoprotein (GPIR). Fragments, subunits, muteins, mimetics, variants and/or analogues of such toxins are, of course, known to those of skill in the art and are encompassed by the invention. It is contemplated that all such variants or mutants which retain their toxic properties will be of use in accordance with the present invention.

Methods of selecting toxins and binding (e.g., associating, attaching or conjugating) them with a targeting moiety (e.g., a peptide or antibody), are routine and conventional in the art. See, e.g., U.S. Pat. Nos. 5,840,522; 5,079,163; 4,520,011; 5,667,786; 5,686,072; 4,340,535; 6,020,145; 5,254,342; 4,911,912; 4,450,154; and 5,928,873. Methods of attaching a peptide or polypeptide toxin to, e.g., a peptide or antibody targeting moiety, include, for example, covalent binding, affinity binding, intercalation, coordinate binding and complexation. Covalent binding can be achieved either by direct condensation of existing side chains or by the incorporation of external bridging molecules. Many bivalent or polyvalent agents are useful in coupling protein molecules to other proteins, peptides or amine functions, etc. For example, the literature is replete with coupling agents such as carbodiimides, diisocyanates, glutaraldehyde, diazobenzenes, and hexamethylene diamines. In some embodiments, one may first wish to derivatize the targeting moiety and then attach the toxin component to the derivatized product. Suitable cross-linking agents for use in this manner include, e.g., SPDP(N-succinimidyl-3-(2-pyridylthio)propionate) and SMPT (4-succinimidyl-oxycarbonyl-α-methyl α(2-pyridylthio)toluene). In one embodiment, a toxin and a targeting moiety can be covalently bonded by forming a disulfide bond between naturally occurring free thiol groups (e.g., in the A chain of a ricin) and/or a thiol or activated disulfide group which has been introduced into an analogue of a peptide chain (e.g., an analogue of gelonin having a cysteine available for disulfide bonding).

In another embodiment, the therapeutic moiety can comprise any of a variety of art-recognized radioisotopes or radionuclides. Methods of radiotherapy (nuclear medicine), in which cytotoxic doses of radioactivity are delivered to cells, are conventional in the art and are described, e.g., in EP 481,526; U.S. Pat. No. 5,962,424; Roeske et al (1990). *Int. J. Radiation Oncology Biol. Phys.* 19, 1539-48; and Lerchner et al (1993). *Med. Phys.* 20 (2 Pt. 2), 569-77. Such radioactive compounds can affect the targeted cell as well as adjacent tumor cells which, for one reason or another, do not display Hsp47 on their surface. Further disclosure of the types of radioactive agents which can be used, and how to attach them to targeting moieties, is discussed below in reference to imaging agents. Among the most preferred radiation sources are Tc-99 and In-111.

In another embodiment, the therapeutic moiety can comprise an antibody, and can be used as a basis for conventional types of immunotherapy, e.g., as discussed below in regard to antibodies that are not associated with an additional therapeutic moiety.

Of course, combinations of the various therapeutic moieties can be coupled to one targeting moiety, thereby accommodating variable cytotoxicity. In another embodiment, two or more different therapeutic agents are administered together.

Many variations of treatment are encompassed by the invention. For example, it may be desirable to treat a patient preliminarily with an amount of a toxin (or other therapeutic agent) effective to generate an immune response, thereby providing systemic protection from the toxin to the patient. Subsequently, one can administer the toxin to the patient in an amount effective to kill tumor cells. See, e.g., U.S. Pat. No. 5,667,786.

In another embodiment, an anti-Hsp47 antibody which is not associated with an additional therapeutic moiety can be used to treat, e.g., a carcinoma, in a method of immunotherapy. Any of the types of antibodies described herein as targeting moieties can be used for immunotherapy. Methods of immunotherapy are conventional and are described, e.g., in U.S. Pat. Nos. 6,015,567, 5,478,556 and 6,017,540.

In one such embodiment, the antibody brings about an effect by virtue of its association with Hsp47 on the cell surface. Example 3 demonstrates that cell surface localized Hsp47 is associated with the tetraspanin protein, CD9, and thus can be involved in the interaction of cells with the cellular matrix. Therefore, an antibody directed against Hsp47 can modulate the interaction of a cell, e.g., a carcinoma cell, with the intracellular matrix. Furthermore, cell surface expression of Hsp47 can be correlated with cell invasiveness and phagokinesis (mobility) which, in turn, can be correlated with metastatic potential of a carcinogenic cell. Example 4 demonstrates a negative correlation in several cell lines between cell surface expression of Hsp47 and invasiveness/phagokinesis. Without wishing to be held to any particular mechanism, the invention encompasses methods of treatment with an anti-Hsp47 antibody to modulate (increase or decrease a physiological activity or property of) a cell (e.g., carcinoma cell, a tumor, etc.), for example to modulate invasion, migration/motility of tumor (e.g., carcinoma) cells, and/or metastasis of a tumor cell (e.g., carcinoma cell).

In cases in which Hsp47 cell surface expression is negatively correlated with tumor invasiveness and/or metastasis, the detection of surface-expressed Hsp47 can serve as the basis of a diagnostic method to identify tumors (e.g., carcinomas) which are substantially non-metastatic and/or which are associated with a better prognosis than tumors on whose surface the expression of Hsp47 is substantially lower.

In another such embodiment, the antibody can elicit an immunological effect. Without wishing to be bound by any particular mechanism, the invention encompasses situations in which an antibody recruits NK cells for antibody-mediated cell-mediated cytotoxicity. Bifunctional antibodies can bring effectors such as NK and $T_c$ close to the tumor target. Many variations of immunotherapy will be evident to those of skill in the art. For example, two bispecific heteroantibodyconjugates, e.g., anti-tumor/anti-CD3 and anti-tumor/anti-CD28, can be co-administered. Without wishing to be bound by any particular mechanism, it is proposed that two such heteroconjugates can act synergistically to induce contact between a T-cell and a tumor to activate direct cytotoxicity even if the T-cell, itself, does not have conventional specificity for the tumor target.

Immunotherapy can be carried out by introducing an antibody directly into a patient, using conventional delivery methods and doses, such as those described herein for other therapeutic agents. Alternatively, one or more external domains of Hsp47, or fragments thereof, which contain an immune epitope can be introduced into a patient as a vaccine, in order to elicit a cell-mediated immune response. In a preferred embodiment, the external domain is "isolated," e.g., is essentially free of transmembrane and cytoplasmic domains. The external domain or fragment thereof can be of any size, providing it comprises at least one immunoepitope. If desired, the external domain can be co-administered with, or conjugated to, one or more other reagents which can enhance the immune response, e.g., a costimulatory molecule such as B7 or cytokines IFNγ, GMCSF, L2/4 and 7; an antigenic molecule, such as a peptide; or a suitable adjuvant.

In another embodiment, a bacteriophage whose surface comprises a peptide which is specific for Hsp47 can serve as a vector for the implementation of gene therapy Typical methods of phage display and affinity panning designed to obtain phage which can be used in such a method are described herein. A gene whose expression in a mammalian host is desired can be inserted into a mammalian expression cassette and then cloned into the phage genome. Cassettes for mammalian gene expression are conventional in the art, as are methods for cloning such cassettes into a nucleic acid of interest, e.g., the DNA of a filamentous phage. Methods to clone and express genes are routine for one of ordinary skill in the art. See, e.g., Sambrook, J. et al (1989). *Molecular Cloning, a Laboratory Manual*. Cold Spring Harbor Laboratory Press, Cold Spring Harbor, N.Y.; Ausubel, F. M. et al (1995). *Current Protocols in Molecular Biology*, N.Y., John Wiley & Sons; and Davis et al. (1986), *Basic Methods in Molecular Biology*, Elsevir Sciences Publishing, Inc., New York. In particular, methods of using phage as gene delivery vehicles for mammalian cells are conventional and are described, e.g., in Larocca et al (1999). *FASEB Journal* 13, 727-734; Barry et al (1996). *Nat. Biotechnology*, 1282, 7711; Larocca et al (1998). *Hum. Gene Ther.* 9, 2393-2399; Poul et al (1999). *J. Mol. Biol.* 288, 203-11; and Kassner et al (1999). *Biochem. Biophys Res. Comm.* 264, 921-8.

For many of the molecular biology techniques referred to in this application, including isolating, cloning, modifying, labeling, manipulating, sequencing, and otherwise treating or analyzing nucleic acid and/or protein, see, e.g., Hames et al. (1985), *Nucleic Acid Hybridization*, IL Press. Dracopoli, N.C. et al., *Current Protocols in Human Genetics*, John Wiley & Sons, Inc.; and Coligan, J. E. et al., *Current Protocols in Protein Science*, John Wiley & Sons, Inc.

Any of a variety of therapeutic genes can be introduced into a cell, in a method of gene therapy, with such a vector. Such genes can be translated into proteins, expressed as antisense nucleic acid sequences or ribozymes, or the like. The genes can be integrated into the host genome, or can be stably maintained or transiently expressed in an unintegrated form.

The types of genes which can be administered are well-known in the art and are disclosed, along with methods of using them for gene therapy, in, e.g., Culver et al (1994). TIG 10, 1744-178 and U.S. Pat. Nos. 6,017,896; 5,916,803; 5,871,726; 5,688,773; 5,496,731; 5,631,236; 5,962,424; 5,922,685; 5,789,244; 5,662,896; 5,532,220; 5,888,502; 5,888,814; 5,932,210; and 5,916,803. The genes can be introduced into cells ex vivo and reintroduced into a patient, or introduced in viva. Among the general classes of genes which can be administered are: genes which enhance the immunogenicity of a tumor, e.g., genes which encode foreign antigens; genes which initiate apoptosis; genes which enhance immune cells to increase anti-tumor activity, e.g., genes which encode cytokines, such as IL-1, IL-2, IL-4, IL-6, IL-12, TNF-α or β; GM-CSF, G-CSF, M-CSF, IFN-α, β or γ, TGF-α or β, TNF-α or β, NGF or the like; sensitivity or suicide genes (e.g., genes which encode HSV- or VZV-Tk, which confer sensitivity to gancyclovir; or which encode cytosine deaminase, which confers sensitivity to 5-fluorocytosine; or which encode a non-human purine cleavage enzyme, such as purine nucleoside phosphorylase, which confers sensitivity to a purine substrate which, when cleaved by the enzyme, becomes toxic to the cell); genes which block the expression of oncogenes, e.g., genes which encode antisense K-RAS message); wild type tumor suppressor genes (e.g., p53; p16; retinoblastoma (RB)gene, either full-length $p110^{RB}$ or mutant proteins such as $p94^{RB}$ or $p56^{RB}$; mitosin; or H-NUC); genes which block the mechanisms by which tumors evade immunological destruction, e.g., the gene which encodes antisense IGF (insulin-like growth factor)-1 message; genes which encode an engineered cytoplasmic variant of a nuclease (e.g., RNase A) or protease (e.g. trypsin, papain, proteinase K, carboxypeptidase, etc.); and genes which encode any of the proteinaceious toxins disclosed above.

Many other types of gene therapy are encompassed by the invention and will be evident to one of ordinary skill in the art. For example, any targeting moiety as above can be associated with (e.g., bound to, covalently or noncovalently) a gene of interest and can serve to deliver it to a cell. In one embodiment, the targeting moiety comprises part of a vector which also comprises one or more of: a) a non-viral carrier for the gene to be inserted; b) a fusion protein to enhance the penetration of the vector into the cytoplasm and, optionally, the nucleus, of the cell; and c) a therapeutic gene such as those described above in reference to bacteriophage-mediated gene therapy. Many varieties of components a) and b) will be known to those of skill in the art. For a further discussion of these components, see, e.g., in U.S. Pat. No. 5,916,803 and the section below regarding the introduction of peptides and similar agents into a cell.

Methods to deliver (administer, introduce) therapeutic agents into a cell, tissue or tumor, or into a patient, in vitro or in vivo, and to monitor the effects so induced, will be evident to one of ordinary skill in the art. See, e.g., references cited herein, and Vitetta et al (1991). *Cancer Res.* 51, 4052. Agents to be administered in vivo can be formulated with pharmaceutically acceptable carriers, excipients or vehicles and, in addition, can be supplemented with other medicinal agents such as, e.g., adjuvants, stabilizers, enhancers, or the like.

The specificity of targeting which is engendered by the invention allows for systemic administration. Alternatively, agents can be administered at or near the site of a tissue or tumor to be treated. (Of course, the routes of administration disclosed herein can be employed for methods of detecting (imaging) a target as well as for methods of treatment.). Methods of administration are conventional, and include parenteral and non-parenteral routes of administration. Parenteral routes include, e.g., intravenous, intraarterial, intraportal, intramuscular, subcutaneous, intraperitoneal; intraspinal, intrathecal, intracerebroventricular, intracranial, intrapleural or other routes of injection. Non-parenteral routes include, e.g., oral, nasal, transdermal, pulmonary, rectal, buccal, vaginal, ocular. For non-parenteral delivery, it may be desirable to use agents which enhance transcytosis of a cell-surface receptor/ligand complex, e.g. by administration of brefeldin A or monensin. See, e.g., U.S. Pat. No. 5,254,342.

Dosages to be administered can be determined by conventional procedures and, in general, will be known to those of skill in the art. Factors to be considered include the activity of the specific agent involved, the metabolic stability and length of action of the agent, mode and time of administration, drug combination, rate of excretion, the species being treated, and the age, body weight, general health, sex, diet, and severity of the particular disease-states of the host undergoing therapy. For example, appropriate therapeutic regimens for an immunotoxin (i.e., a conjugate comprising an antibody, or variant or fragment thereof, conjugated to one or more toxin molecules) involve administration to a patient of a dose of between about 0.5 and 2 mg/kg.

A therapeutic agent can be internalized into any of a variety of locations in a cell or tissue. In some cases, it is desirable that a therapeutic agent is internalized into a cell by accompanying Hsp47 as it is recycled into the ER. In other cases, it is desirable that a therapeutic agent is endocytosed into an endosome or lysosome of a cell, e.g., a proteinacious toxin which must be proteolytically processed in order to become active. In still other cases, it is desirable that the agent evades enzymatic degradation and is transported into the cytoplasm and/or the nucleus. A variety of conventional procedures can be used to enhance the transport of a surface-bound entity into a cell and, in some cases, to avoid such proteolysis. It may be desirable, for example to associate the therapeutic agent, directly or indirectly, with a carrier and/or with a fusion protein, to generate a vector for delivery of the therapeutic agent.

A variety of appropriate carriers (e.g., non-viral carriers) are well-known in the art and are described, e.g., in U.S. Pat. No. 5,916,803; Cotten et al (1993). *Curr. Biol.* 4, 705; Behr (1993). *Acc. Chem. Res.* 26, 274; Felgner (1990). *Adv. Deliv. Rev.* 5, 163; Behr (1994). *Bioconjugate Chem.* 5, 382; and Ledley (1995). *Hum. Gene Ther.* 6, 1129. In a preferred embodiment, the carrier exhibits a long half life in the body, allowing the maximum possible binding of a vector to a target cell. Among the preferred carriers are liposomes or cationic lipids, polypeptides, or proteins, or the like. A carrier can be associated directly (e.g., coupled) or indirectly to a therapeutic agent, by any of a variety of conventional means.

A variety of fusion proteins can enhance the penetration of a vector into a cell, and/or out of an endosome or lysosome and into the cytoplasm of a cell. Many proteins, or fragments or variants thereof, possess fusiogenic properties, including a number of viral proteins. Such proteins will be well known to the skilled worker and are discussed, e.g., in U.S. Pat. No. 5,916,803; Hughson (1995). *Current Biol.* 5, 265; Iloekstra (1990). *J. Bioenergetics Biomembranes* 22, 675; and White (1990). *Ann. Rev. Physiol.* 52, 675.

In some cases, a targeting moiety can be modified so that it binds more efficiently to an external domain of Hsp47 and/or is internalized more efficiently into a cell. For example, synthetically produced short peptides, such as some of the 7-mer peptides shown in Table 3, sometimes bind to, but are not taken up by, target cells; whereas the same peptides are internalized when they are displayed at the pIII terminus of a bacteriophage. To enhance the internalization of, e.g., a short synthetic peptide, one can add to the peptide a synthetic peptide linker having desirable properties, e.g., a linker which displays the short peptide in such a way that it can bind to and be internalized by a cell with Hsp47 on its surface, yet does not, itself, bind to cells other than those displaying Hsp47 on the surface; is stable in the circulation; can be processed following internalization, or the like. Other such improvement modifications of target moieties will be evident to those skilled in the art.

In another aspect of the invention, a targeting moiety as above is associated with a detectable moiety that allows the detection (imaging, identification) of a cell which expresses Hsp47 on its surface, e.g., a carcinoma cell, a carcinoma in any stage of development, a tumor, a metastasis (including a micrometastasis), or the like. An agent which comprises a targeting moiety and a detectable moiety is called herein a detectable agent or an imaging agent. Such detection can be accomplished in vitro or in vivo. Detection methods can be quantitative. For example, the amount of Hsp47 expressed on the surface of a cell, or the number of cells which express Hsp47 on their surface, can be quantitated by exposing the cell, tumor, animal, patient or the like to a detection device which can identify and quantitate the detectable marker.

Detectable moieties encompassed by the invention include, e.g., signal generators [entities which are capable of emitting a detectable amount of energy in the form of electromagnetic radiation (such as X-rays, UV-radiation, IR radiation, visible radiation and the like), and include phosphorescent and fluorescent entities, bioluminescent markers, gamma and X-ray emitters, or the like]; signal reflectors (e.g., paramagnetic entities); or signal absorbers (e.g., electron beam opacifier dyes).

A detectable moiety can be bound to (associated with) a targeting moiety by any of a variety of well-established methods, including those described above for binding therapeutic moieties to targeting moieties. For example, in methods particularly suited for in vitro detection, a radioactive element (e.g., an amino acid) can be incorporated directly into a targeting moiety (e.g., a peptide chain), and detected by autoradiography; or a fluorescent label can be associated with such a targeting moiety via biotin/avidin interaction, association with a fluorescein conjugated antibody, or the like, and detected by immunofluorescence microscopy, flow cytometry (FACscan), or the like.

Target-enhancing metals are encompassed by the invention and are particularly suitable for in vivo imaging. Metals according to the invention include, e.g., paramagnetic metals for MRI; heavy metal ions, e.g., with atomic numbers of at least 37, preferably at least 50, for X-ray or ultrasound imaging; and ions of radioactive isotopes for scintigraphy. The choice of metal will be determined by the desired diagnostic (or therapeutic) application. Examples of radioactive ions include, e.g., ions of lanthanides or other metal ions, including isotopes and radioisotopes thereof, such as, e.g., iodine$^{123}$, iodine$^{125}$, iodine$^{131}$, technicium$^{99m}$, indium$^{111}$, rhenium$^{188}$, rhenium$^{186}$, copper$^{67}$, yttrium$^{90}$, astatine$^{211}$, gallium$^{67}$, iridium$^{192}$, cobalt$^{60}$, radium$^{226}$, gold$^{198}$, cesium$^{137}$, phosphorous$^{32}$, carbon$^{14}$, and tritium ions. Examples of fluorogenic agents include gadolinium and renagraphin.

A metal can be associated with a targeting moiety by any of a variety of means, which are well-known to one of ordinary skill in the art. For methods of making image enhancing moieties, attaching them to targeting moieties, and using them for detection, see, e.g., EP 481,526; GB-A-2169598; and EP 136,812. For example, metals can be bound to (associated with, attached to) targeting moieties by chelating agents, including polychelants, bifunctional polychelants, and salts or macrocyclic intermediates thereof. A variety of methods exist for multiplying the enhancement, e.g., using a compound composed of a backbone molecule, such as a polyamine, to which a plurality of chelating agents are attached.

Routes by which imaging agents can be administered are disclosed above with reference to delivering therapeutic agents. Imaging agents of the invention may be administered to patients for imaging in amounts sufficient to yield the desired contrast with the particular imaging techniques. Generally, dosages of from about 0.001 to 5.0 mmoles of chelated imaging metal ion per kilogram of patient body weight are effective to achieve adequate contrast enhancements. For most MRI applications, preferred dosages of imaging metal ions will be in the range of about 0.02 to 1.2 mmoles/kg body weight; while for X-ray applications, dosages from about 0.5 to 1.5 mmoles/kg are generally effective to achieve X-ray attenuation. Preferred dosages for most X-ray applications are from 0.8 to 1.2 mmoles of the lanthanide or heavy metal/kg body weight.

Another aspect of the invention is a method to screen for an agent which binds specifically to a carcinoma in which Hsp47 is expressed on the surface of at least some of its cells, preferably wherein the agent is useful for treating a carcinoma in a patient or for diagnosing a carcinoma in a patient, comprising identifying an agent which binds specifically to an external domain of Hsp47. Assays for determining if an agent binds to an external domain of Hsp47, and for determining the specificity and/or avidity of the binding, are described elsewhere in this application. Routine procedures are available for screening agents of interest, using such methods.

Another aspect of the invention is a kit for treating a patient suffering from a carcinoma in which Hsp47 is expressed on the surface of at least some of the carcinoma cells, or for detecting a carcinoma in which Hsp47 is expressed on the surface of at least some of the carcinoma cells, comprising an agent which binds specifically to an external domain of Hsp47 in an amount effective to generate a cytostatic or cytolytic effect on the carcinoma, or to image the cell above a background of non-carcinoma cells. In a preferred embodiment, the agent comprises, as a targeting moiety, an antibody or a fragment thereof, a peptide, or a bacteriophage on whose surface is a peptide, each of which moieties binds specifically to an external domain of Hsp47. In a most preferred embodiment, the targeting moiety is a monoclonal antibody, a peptide which comprises the consensus motif XHy-HyXXHyXXXXHyHy (SEQ ID NO: 1) or the consensus motif HyXXXHyHyXXHyXXX (SEQ ID NO: 2), wherein X, independently, can be any amino acid, and Hy, independently, can be any hydrophobic amino acid, a peptide having the sequence of any of SEQ ID NO:3 to SEQ ID NO: 25 of Tables 1 and 2, or a bacteriophage on whose surface is a peptide which binds specifically to an external domain of Hsp47.

In one embodiment, the agent comprises, as a therapeutic moiety, a toxin, a radioisotope or radionuclide, an antibody, or a nucleic acid which encodes a therapeutic gene. The invention also encompasses a kit for modulating a cell which expresses Hsp47 on its surface, comprising an agent which binds specifically to an external domain of Hsp47, in an amount effective to modulate the cell. Of course, a kit of the invention will comprise one or more containers for the therapeutic and/or imaging agents.

EXAMPLES

Data which are disclosed in the following Examples 1-6 are presented in the manuscripts: 1) Hebert et al. (1999). *J. Cellular Biochemistry* 73, 248-258, which is incorporated by reference in its entirety; and 2) Sauk et al. (2000). *J. Cellular Biochemistry*, accepted in January, 2000, which is included herein as Appendix I and is incorporated by reference in its entirety.

Example 1

Expression of Colligin/Hsp47 at the Surface of Oral Epidermoid Carcinoma Cells

Studies are performed using established cell lines of human oral squamous cell carcinomas (SCC-4, SCC-9, SCC-15, and SCC-25) and a murine epidermoid cell line, Lewis Lung Carcinoma (LL/2), obtained from ATCC. In addition, a primary gingival fibroblast cell line is used as a control.

A. Flow Cytometric Analysis:

For these studies, the monoclonal antibody SPA-470 to colligin/Hsp47, (StressGen, Victoria, BC) and a colligin/Hsp47 rabbit polyclonal antibody, prepared against a 22-mer peptide corresponding to the N-terminal sequence of mouse colligin/Hsp47, are used. Monoclonal antibodies for cytometric analyses are directly conjugated with fluorescein using 5(6) carboxyfluorescein-N-hydroxy succinimide ester kit (Boehringer Mannheim, Indianapolis, Ind.) or labeled with SA-Red670™ following biotinylation of the antibody using EZ-Link™ Sulfo-NHS-LC-Biotinylation kit (Pierce, Rockville, Ill).

Cells grown in vitro are washed and incubated in a 0.5% solution of Polyglobin N to block unsaturated Fc receptors and reduce non-specific binding of monoclonal antibodies. Next, 50 ml of the cell suspension ($1\times10^6$ cell/ml) is incubated with 2.5 ml (1 mg) of antibodies, conjugated with fluorescein, or SA-Red670™ (GibcoBRL, Gaithersburg, Md.). After washing, the cell pellet is resuspended in PBS containing BSA for flow cytometric assay. To assess intracellular colligin/Hsp47, cells are first permeabilized with 0.1% Saponin. Samples are then analyzed on a FACScan flow cytometer (Becton Dickinson, San José, Calif.). The 488 nm Argon laser is run at 15 nW of power. The data from fluorescein conjugates are collected after a 530/30 BP filter. For two-color flow cytometric analysis either fluorescein or Red670™ are employed with propidium iodide. The filters used are 600 mm dichroic SP; 525±15 nm BP (fluorescein) and 645 LP (Red670™).

Propidium iodide is used to assess cell cycle and stain for dead cells. For these studies a hypotonic citrate solution containing PI is added to ~$1\times10^6$ washed cells to a concentration of 1 mM. Cells are labeled for 20 minutes, then analyzed on the FACScan in their staining solution. Orange PI fluorescence is collected after a 585/42 nm BP filter.

Electronic compensation is used among fluorescence channels collecting emissions to remove residual spectral overlap. Fluorescence data are displayed on a four-decade long scale. A minimum of 10,000 events is collected on each sample. Analysis of the data is performed with LYSYS II software (Becton Dickinson, Mansfield, Mass.). Fluorescence dual parameter contour plots are used for exclusion of debris and clumps. This method of gating allows ready discrimination of debris from dead cells (low forward light scatter and high PI fluorescence). The percentage of cells with a $G_{1/0}$, S, of $G_2/M$ DNA complement is determined from a DNA histogram by region integration using onboard Multicycle® data analysis routines (Phoenix Flow Systems, San Diego, Calif.).

Flow-cytometric analysis of SCC cell lines, the LL/2 murine cell line and human gingival fibroblasts reveals that all of the cell lines possess intracellular colligin/Hsp47. Cell cycle analysis further reveals that colligin/Hsp47 expression is not limited to any phase of the cell cycle in either gingival fibroblasts or epidermoid carcinoma cells. However, when cell cycle analysis is performed only for cell surface expression, colligin/Hsp47 is only limited to epidermoid carcinoma cell lines.

B. Immunofluorescence Studies: Immunofluorescence microscopy is carried out after the method of Tang et al. (Tang et al. (1994). *Eur. J. Cell Biology* 65, 298-304: Tang et al. (1993). *Eur. J. Cell Biology* 120, 325-328). To visualize cell surface colligin/Hsp47, the cells are not permeabilized but treated and fixed with 1% paraformaldehyde as described for cytometric analyses. The cells are then stained with anti-colligin/Hsp47 antibodies as a primary antibody followed by FITC goat-anti-rabbit or anti-mouse IgG.

Immunofluorescence microscopy of non-permeabilized cells, prepared for flow-cytometric analysis, confirms anti-colligin/Hsp47 staining at the surface.

C. Subcellular Membrane Fractionation: The method for fractionating plasma membranes is modified after the methods described by Weber et al. (1988). "Subcellular distribution of Insulin Receptors" in *Insulin Receptors*. Kahn C R and Harison L S, eds. (New York: Alan R. Liss, Inc), pp. 171-187. In essence, after incubating 5 ml of cells [(2–5)× $10^6$ cells per ml] with or without 1 mM amiloride, the cell suspension is centrifuged at 100 g for 60 s at room temperature. The cell pellets are suspended in 10 ml of tris/EDTA/sucrose buffer (20 mM Tris/HCl, 1 mM EDTA and 255 mM sucrose, pH 7.4) at 18-20° C. The pellet is resuspended in 500 µl of Tris/EDTA/sucrose buffer by using a glass-Teflon homogenizer, layered on a 600 µl cushion of 1.2 M sucrose in 20 mM Tris/1 mM EDTA buffer (pH 7.4), and centrifuged in a Beckman TLS55 rotor at 8,150 g at 4° C. for 30 min. Plasma membranes collected at the cushion interface are suspended in 2.5 ml of Tris/EDTA/sucrose buffer and centrifuged in a Beckman TLA100.3 rotor at 410,000 g at 4° C. for 20 min. The final plasma membrane pellet is resuspended in 60 µl of buffer. The samples are then treated with bacterial collagenase to eliminate the possibility of cytoplasmic derived procollagen-colligin/Hsp47 binding to the cell surface integrin receptors as a result of cell fractionation. The initial supernatant is centrifuged in a Sorvall SS34 rotor at 48,000 g at 4° C. for 15 min. and the high-density microsome pellet is resuspended in 40 µl of buffer. The supernatant is further centrifuged in a Beckman 70.1 rotor at 300,000 g at 4° C. for 75 min. and the low-density microsome pellet is resuspended in 60 µl of buffer.

The membrane fractions are characterized by the distribution of 5'-nucleosidase activity, a marker of plasma membrane. Protein is measured with the BCA protein assay kit (Pierce, Rockford, Ill.). Plasma membranes are directly subjected to PAGE and Western analysis. For Western blots, proteins run on SDS-PAGE are immediately electrotransferred to nitrocellulose paper and blocked with 10% NFDM in 10 mM Tris-HCl pH 7.4, 0.9 mMNaCl (TBS) for 2 hr and then in TBS/NFDM with 2% NGS (GIBCO, Grand Island, N.Y.). Antiserum or perimmune serum is diluted 1:2000 in the same buffer and incubated with gentle shaking overnight. The nitrocellulose is then rinsed three times for 5 min. in TBS/Tween. Hsp47 is detected with [$^{125}$I]-labeled protein A (New England Nuclear, Boston, Mass.).

Subcellular membrane fractionation of amiloride and control cells to obtain a plasma membrane fraction, followed by Western blot analysis confirms the presence of colligin/Hsp47 in the plasma membrane 5'-nucleosidase fraction.

Example 2

Binding of Cell Surface Colligin/Hsp47 to α1 (I)-N-Propeptide

The cDNA sequences encoding the pro α1 (I) N-propeptide globular domain (NP1) [residues 23-108], and the globular domain+propeptide GlyXaaYaa domain (NP2) [residues 23-151] are prepared as GST-fusion proteins as previously described (Hu et al. (1995). *Cellular Biochemistry* 59, 350-367). Fusion protein expression is induced by 0.1 mM IPTG after bacteria reach mid-log phase. The fusion proteins are purified by glutathionine-Sepharose 4B beads (Pharmacia, Piscataway, N.J.) according the manufacture's instructions. The proteins are characterized by SDS-PAGE and Western blot analysis as previously described (Hu et al., ibid).

NP1 and NP2 affinity beads are prepared, after the method of Hu et al. (1995) ibid. In essence, GST-fusion proteins are treated with thrombin, dialyzed and the GST protein removed from each reaction mixture by passing it over a column of glutathione-Sepharose. The eluates are collected and lyophilized and coupled to CNBr activated Sepharose. The final beads contain 1-2 mg peptide per 250 µl. Hsp47 surface binding experiments are carried out by mixing 250 µl of a 50% (v/v) suspension of peptide-Sepharose (Pharmacia, Piscataway, N.J.) with a suspension of plasma membranes from surface-biotinylated SCC cells. After incubation at 4° C. for 1 h the beads are collected by centrifugation and washed 3 times with an equal volume of Laemmli Buffer. The beads are extracted with 250 µl Laemmli electrophoresis sample buffer by boiling the sample for 5 min. Following separation by SDS-PAGE, the proteins are transferred to nitrocellulose membranes and visualized with HRPO-conjugated ExtrAvidin (Sigma Chemical Co., St. Louis, Mo.) using Renaissance Chemiluminescent Reagents (NEN, Cambridge).

To demonstrate the availability of cell surface colliginHsp47 to bind procollagen propeptides in living cells, GST-fusion proteins (1 g/ml) are added to the culture medium of ~1×$10^6$ SCC cells, plated in chambered slides (Nalgene NUNC, Milwaukee, Wis.), for 10 minutes at 37° C. The cells are then washed in PBS fixed in paraformaldehyde as before, and cell associated fusion proteins (NP1, NP2) are identified with HRPO-conjugated anti-GST antibodies, following the procedures of Sauk et al., (1994). *J. Biol. Chem.* 269, 3941-3946.

Binding experiments performed with biotin labeled plasma membranes and Sepharose bound pro α1 (1) globular domain (residues 23-108) or pro α1(1) globular domain+propeptide GlyXaaYaa domain (residues 23-151) give similar results. In both instances bands migrating at 46K and 47K are identified. Western blot analysis confirms that both the 46K, unglycosylated colligin/Hsp47, (Hirayoshi et al., 1991) and 47 K bands react with anti-Hsp47 antibodies. These findings are consistent for all of the cell lines.

Immunoperoxide cytochemical staining of GST-fusion proteins bound to cells in culture reveal that cells lines with a higher percentage of cells expressing surface colligin/Hsp47 display a higher percentage of bound GST-NP1 and GST-NP2 fusion proteins.

Example 3

Cell Surface Labeling and Immunoprecipitation

The methods used were previously described for the characterization of TM4SF complexes with integrins (Berditchevski et al., (1996) *Molec. Biol. of the Cell* 7, 193-207). In essence, cells are labeled with NHS-LC-biotin (Pierce, Rockford, Ill.) according to kit protocol, and lysed in immunoprecipitation buffer [1% Brij 96, 25 mM Hepes, pH 7.4, 150 mM NaCl, 5 mM $MgCl_2$, 2 mM PMSF, 20 µg/ml apotinin, and 10 µg/ml leupeptin]. Immune complexes are collected on protein A beads pre-bound with antibodies, followed by four washes with immunoprecipitation buffer. For more "stringent" conditions, the immunoprecipitation buffer is supplemented with 0.2% SDS. Immune complexes are eluted from protein A beads with Laemmli elution buffer and proteins are separated by SDS-PAGE. Proteins are transferred to nitrocellulose membranes and visualized with HRPO-conjugated ExtrAvidin (Sigma Chemical Co., St. Louis Mo.) using Renaissance Chemiluminescent Reagents (NEN, Cambridge). Reprecipitations are preformed from Brij 96 lysates prepared from surface-biotinylated SCC cells. After five washes with the immunoprecipitation buffer, the protein complexes are dissociated with 0.5% SDS added to the immunoprecipitation buffer. The eluates are subsequently diluted 1:1 with immunoprecipitation buffer and re-precipitated with the appropriate antibodies directly coupled to Sepharose beads. The samples are then processed as described above.

For cross-linking, cells are treated with DTSSP, a membrane impermeable cross-linker or DSP. After solubilization in immunoprecipitation buffer supplemented with 0.2% SDS protein complexes are immunoprecipitated as above and analyzed under reducing conditions.

Membrane surface proteins are consistently co-precipitated with anti-colligin/Hsp47 antibodies. In cross-linking studies, SCC and LL/2 cells are first pre-treated with a cleavable cross-linker, DSP, then surface labeled with biotin or $[^{125}]$-I, and subsequent immunoprecipitation is carried out under stringent conditions to disrupt the noncovalent association between Hsp and tetraspanin protein. A colligin/Hsp47-CD9 complex is immunoprecipitated using either anti-CD9 mAbs or anti-colligin/Hsp47 antibodies. A characteristic 47K band is readily detected in all anti-CD9 immunoprecipitates and protein band of 22K, similar in size to CD9/or CD81, is co-precipitated with anti-colligin/Hsp47. However, when similar experiments were performed with anti-CD81 mAbs, colligin/Hsp47 is not identified in the immunoprecipitates. However, re-immunoprecipitation of the CD9 immunoprecipitates with anti-colligin/Hsp47 results in a 47 K band in all SCC cells and LL/2 cell lines. To verify whether extracellular regions of Hsp47 and CD9 interact directly, similar cross-linking experiments are performed using DTSSP, a membrane impermeable cross-linker. Treatment of intact SCC and LL/2 cells with either DSP or DTSSP results in co-immunoprecipitation of CD9 and colligin/Hsp47. Treatment with 1 mM amiloride greatly enhances the amount of colligin/Hsp47 recovered following immunoprecipitation without altering the profile of proteins precipitated.

Example 4

Tumor Cell Invasion and Phagokinesis

A: Colloidal Gold Migration Assay:

Tumor cells are plated on chamber slides precoated with a mixture of 80 µg/ml type I collagen, 100 µg/ml MatrigelR, or 100 µg of laminin-5 and colloidal gold particles and incubated in medium with or without various antibodies. Colloidal gold-coated chamber slides are prepared as described by Albrecht-Buehler ((1977). *Cell* 12, 333-339) with modification for keratinocytes and the inclusion of matrix proteins (Woodley et al., (1988) *J. of Cellular Phys.* 136, 140-146; Kim et al., (1994) *Laboratory Investigation* 71, 401-408; Kim et al., (1994) *J. of Biol. Chem* 269, 26, 926-26, 932.) SCC or LL/2 cells are added to each chamber, and 20 minutes latter non-adherent cells are removed and the medium replaced. Cultures are maintained for 24 hr and then fixed in 1× Histochoice (Amresco, Solon, Ohio) for 1 min, washed in PBS, and dehydrated through graded ethanols. Areas devoid of gold particles identify the phagokinetic tracks. A migration index is determined using image analysis software by measuring the area of phagokinetic tracks associated with cells in random fields under dark field illumination at 100× (Pilcher et al., 1997) *J. Cell Biol.* 137, 1445-1457. All cells in a field are counted and 25 cells are counted for each experiment. For each experiment, all conditions are done in triplicate.

B: Tumor Cell Invasion Assays:

An in vitro assay is modified after that described previously by Chu et al. (1993) *Proc. Natl. Acad. Sci.* 90, 4261-4265, utilizing Matrigel®, a reconstituted basement membrane. In essence, a modified Boyden chamber containing an 8 µm-porosity polyvinylpyrolidone-free polycarbonate filter is precoated with Matrigel® (Collaborative Biomedical Products, Becton Dickinson, Bedford, Mass.). The lower well of the chamber is then filled with serum free medium containing 500 µl of 3T6 cell-conditioned medium as a chemoattractant. The upper well is then seeded with 200 µl of cell suspension at $1.0 \times 10^4$ cells/chamber plus additives as indicated. The chambers are then incubated at 37° C. for 24 hrs. Noninvasive cells are removed from the upper surface of the membrane with a cotton swab and the chamber incubated in 3 ml of Dispase (Collaborative Biomedical Products, Becton Dickinson, Bedford, Mass.) for 2 hours and the reaction stopped with 10 mM EDTA. The resulting cells contained in Matrigel®, as well as the cells in the lower chamber, are counted in a Coulter counter. Data are expressed as the percent invasion through the matrix and membrane relative to the migration through the control membrane. The "Invasion Index" is expressed as the ratio of the percent invasion of a test cell over the percent invasion of a control cell.

Overall treatment and group effects are assessed using an analysis of variance (ANOVA), with post-hoc comparisons based on the Newman-Keuls test ($p<0.05$). The association of mean HSP47 fluorescence labeling with the invasion index is evaluated using the nonparametric Spearman's rank-order correlation coefficient (rho).

Using modified Boyden chambers to assess tumor cell invasion reveals that SCC cells and LL/2 cells show a significant variance in the invasion indices among the cell lines. This variance is associated with the level of colligin/Hsp47 expressed on the cell surface. Chamber assays are then performed where the cells are incubated in the presence of antibodies directed to CD9, CD81 and colligin/Hsp47. Cells incubated in Matrigel® chambers with anti-colligin/Hsp47 result in an increase in the invasion index while incubation with anti-CD9 or anti-CD81 antibodies are without effect and similar to controls. Treatment with amiloride in each instant dramatically decreases the invasion index in all tumor cell lines. However, amiloride treated cells are unaffected by treatment with anti-colligin/Hsp47 antibodies.

The results of SCC cell migration on colloidal gold assays parallel the results obtained from Boyden chamber assays, but are dependent upon whether the colloidal gold contains Matrigel®, collagen, or laminin-5. The phagokinetic migration index of SCC cells is greatest on laminin-5 followed by collagen and Matrigel®. In particular, the migration tracks are broader and longer on laminin-5 coated colloidal gold than those observed on collagen or Matrigel®. The phagokinetic migration indices on both collagen and Matrigel® matrices are noted to increase following treatment with anti-colligin/Hsp47 antibodies, but are unaffected following treatment with ant-CD9 antibodies. The phagokinetic indices are unaffected following treatment with anti-colligin/Hsp47 on laminin-5 coated surfaces.

Example 5

Identification and Analysis of Hsp47-Binding Peptides

A. Affinity Panning of a Library of Peptides: Two bacteriophage libraries, with random septapeptide (Ph.D.-7, New England Biolabs; Beverly, Mass.) or random dodecapeptide (Ph.D.-12, New England Biolabs; Beverly, Mass.) inserts at the N-terminus of pIII protein are used. The Ph.D.-7 library consists of ~2.8×10$^9$ electroporated sequences amplified once to yield 70 copies of each sequence in 10 µl of supplied phage. The Ph.D.-12 library consists of ~2.7×10$^9$ electroporated sequences amplified once to yield ~55 copies/10 µl of supplied phage.

B. Selection of Hsp47-Binding Bacteriophages by Affinity Panning:

Bacteriophages displaying peptides recognized by Hsp47 are identified using the Ph.D.-7 or Ph.D.-12 kits and protocols modified for a biotinylated target. In essence, 96 wells of a microtitration plate are coated with 15 µl of streptavidin (1 mg/ml) in 135 µl of 0.1 M NaHCO$_3$ pH 8.6, with gentle agitation in a humidified chamber overnight at 4° C. After removal of the streptavidin solution the wells are washed three times with TBS containing 0.05% Tween 20 (TBS-Tween) and then blocked by incubation for 1 hr at 37° C. with 1% BSP in PBS containing 0.1 µg/ml streptavidin.

Next, phage are precomplexed with biotinylated Hsp47 by adding 0.1 µg biotinylated Hsp47 and 2×10$^{11}$ pfu of the input phage in 400 µl TBS-Tween and incubated for 60 min. The phage-target complex solution is then added to the washed blocked plates and incubated at room temperature for 10 min. Biotin is added to a final concentration of 0.1 mM and incubated for 5 min. to displace streptavidin-binding phage. Non-binding phage are discarded and the plates washed 10× with TBS-Tween (0.1%). The wells are then treated with 15 µl of 1 M Tris-HCl; pH 2.2, containing 1 mg/ml BSA for 5 minutes to elute Hsp47-phage. The samples are neutralized with 1 M Tris-HCl; pH 9.1, and amplified by adding to 20 ml of ER 2537 culture incubated at 37° C. with vigorous shaking for 4.5 hrs. The cultures are then transferred to fresh tubes centrifuged at 10,000 rpm, 4° C., for 10 mins. The supernatants are transferred to fresh tubes and phage precipitated with ⅙ volume of PEG/NaCl at 4° C., overnight. To 4 ml of LB media a single colony of ER2537 is inoculated and then incubated at 37° C. with vigorous shaking until the culture reaches mid-log phase (O.D.$_{600}$ ~0.5). A pellet is obtained by centrifugation for 15 min at 10,000 rpm, 4° C. The pellet is suspended in 1 ml of TBS and centrifuged for 5 min, 10,000 rpm, 4° C. The supernatant is transferred to a fresh tube and precipitated with ⅙ volume of PEG/NaCl on ice for 1 hr. Following centrifugation the pellet is resuspended in 200 µl TBS. The eluate is titered and plated onto LB/IPTG/XGal plates and incubated overnight. Since the library phage are derived from the common cloning vector M13mp19, which carries the lacZα gene, phage plaques appear blue when plated on media containing Xgal and IPTG. Blue colonies are selected for sequencing or used for a second round of panning. As a control streptavidin is used as a target and after three round of panning to verify a consensus sequence for streptavidin-binding peptides.

C. Screening for Hsp47-Binding Bacteriophages:

Clones of blue colonies from plates containing 50-200 colonies are transferred to nitrocellulose filters. The bacteria are washed from the filters with PBS containing 0.05% Tween 20 and 1% bovine serum albumin, and the filters are then incubated for 30 min in the same buffer before washing three times with PBS-Tween. Following incubation for 1 hr in 5 ml of biotinylated Hsp47 (0.1-2 µg/ml in PBS-Tween), the filters are again washed three times in PBS-Tween. The positions of the clones that have secreted Hsp47-binding bacteriophages are then located by one of two methods: the filters are incubated with 5 ml of alkaline phosphatase-conjugated streptavidin (¹⁄₁₀,₀₀₀ dilution in PBS-Tween; Pierce, Rockford, Ill.) for 1 hr at room temperature before extensive washing with PBS-Tween, or the filters are incubated for 1 hr in 5 ml of an anti-biotin antibody (¹⁄₅₀,₀₀₀ dilution in PBS-Tween; Pierce, Rockford, Ill.), washed, and incubated with a rabbit anti-goat immunoglobulin antibody conjugated to alkaline phosphatase (¹⁄₅,₀₀₀ dilution in PBS-Tween; Pierce, Rockford, Ill.). In each case, alkaline phosphatase activity is revealed using a mixture of nitroblue tetrazolium/and 5 bromo-4-chloro-3-indolylphosphate tolidium (Bethesda Research Labs, Rockville, Md.) as substrate.

D. Determination of the Sequence of Bacteriophage-Displayed Peptides:

Single-stranded bacteriophage DNAs are purified and sequenced as −96 primer an oligonucleotide (5'-CCCTCAT-AGTTAGCGTAACG-3') (SEQ ID NO: 63). Sequencing reactions are carried out using an ABI Prism Model 373 Version 3.0.

E. Program to Score Hsp47-Binding Peptides:

The starting and selected libraries are compared in a position-dependent manner. A statistical analysis is performed by maximum likelihood and bootstrap resampling. This reveals the distribution of residues by position in Hsp47-binding peptides compared to peptides in the original library. To codify the preferences obtained above we use a scoring system previously described for BiP (Cwirla et al. (1990) *Proc. Natl. Acad. Sci.* 87, 6378-82) to predict Hsp47-binding sites in synthetic and naturally occurring polypeptides. In so doing a score is given to each of the possible 20 amino acids at each position of the seven-residue core sequence. These scores are derived from the fold difference in the overall abundance of each residue in the peptides displayed by the selected and nonselected bacteriophage populations. The scoring for each of the seven-residue sequences present in each septapeptide is determined as previously described (Cwirla et al., ibid).

To validate the scoring set of Hsp47-binding sequences, a second set of Hsp47-binding sequences not part of the database used to generate the scoring matrix is necessary. To accomplish this a second library consisting of independent recombinant bacteriophages displaying random dodecapeptides is used (Ph.D-12, New England Biolabs, Beverly, Mass.). Sequences are then compared by position specific iterated BLAST, pattern Hit Initiated BLAST, and BLAST 2 sequences against each other (NCBI). In addition, the hydropathic profiles of two peptides are compared using the Weizmann Institute of Sciences Genome and Bioinformatics database.

F. Analysis of the Hsp47-Binding Peptides

Two bacteriophage libraries with random septapeptide or dodecapeptide inserts at the N-terminus of pIII protein are used; the first to be studied is the septapeptide library. 70 individual bacteriophage clones are picked at random from the unselected library, and the amino acid sequences of the variable septapeptide inserts are deduced from the nucleotide sequences of the corresponding coding region. All amino acids are represented, although their frequencies do not always correspond to those expected from the relative numbers of codons encoding each residue.

The sequences of septapeptides displayed by 54 Hsp47-binding bacteriophages obtained by panning are determined by DNA sequence analysis of the corresponding region of the bacteriophage genome. The peptide sequences from the 54 clones that bound Hsp47 are first considered as a single population and compared with those from the 70 clones picked randomly from the starting library. Tabulation of the hydrophilicities of the Hsp47-binding bacteriophages reveals that two general populations of peptides that are selected by panning. One group of peptides is represented by hydrophilic peptides and the other by a smaller hydrophobic group of peptides.

Comparison of the overall amino acid composition of the two populations, selected and unselected, of septapeptides reveals that asparagme (N) threonine (T), tyrosine (Y) and proline (P) are particularly enriched, while phenylalanine (F), aspartic acid (D), and arginine (R) are significantly depleted. However, when considered individually, the hydrophobic group of peptides is noticeably enriched in tryptophan, and leucine as well as valine and alanine.

The five-residue spacer linking the variable septapeptides to the mature pIII protein contains no enriched residues. Inspection of the selected hydrophobic peptides reveals that a residue motif best described as XHyHyXXXHyHy, where Hy is a large hydrophobic amino acid (usually W,L, or F) and X is any amino acid. This core motif is also identified in selected residue from a Ph.D-12 library represented by a motif XHyHyXXHyXXXXHyHy. The peptide motif described as XXHyHyXXX best describes the selected hydrophilic peptides selected from the library. Interestingly, a similar core motif (HyXXXXHyHyXXHyXXX) can also be identified in selected resides from the dodecapeptide library. However, a small number of peptides are completely lacking in hydrophobic residues although they are selected during panning of Hsp47.

BLAST program analyses are performed to assess the sequence homology between bacteriophage-displayed peptides and procollagen I and the selected dodecapeptides. Little specific homology is observed based on sequence alone. However, when the hydropathic profile of procollagen I (1) is compared with the dodecapeptides obtained from three rounds of panning, using Kyte-Doolittle method of calculating hydrophilicity over a window length of 7, all of the phage displayed peptides are represented by specific regions within the procollagen molecule. Most of the hydrophobic peptides (see Table 1) are localized to regions within the N-propeptide region (residues 59-71) or the C-propeptide region (residues 1344-1445). Conversely, most of the hydrophilic peptides (see Table 2) are localized the regions with the helical region of procollagen (residues: 283-295, 470-482, 666-678, 727-739, 1040-1052, and 1087-1099) with only one peptide localized to a sequence within the N-propeptide region (residues 100-112).

Example 6

Subcellular Localization of Hsp47 Binding Phage (HBP) on Tumor Cells

Studies are performed using the cell lines SCC4, SCC9, SCC15 and SCC25 as described above, and a transformed normal oral keratinocyte cell line GMSM-K which is courtesy of Dr. V. Murrah (UNC, Chapel Hill, N.C.). Breast carcinomas [HTB126, HTB127] and HTB125 normal breast cells are obtained from ATCC. In addition, prostate cell lines PC-3, LNCaP and PZ-HPV are courtesy of Dr. R. Franklin (UM, Baltimore, Md.).

A. Flow Cytometric Analysis: Antibodies against Hsp47 are described above, as are methods of conjugating them with fluorescein or Texas Red. Anti-M13 monoclonal antibody is procured from Amersham Pharmacia Biotech (Piscataway, N.J.). Cytometric analysis is conducted as described above.

25 µl of HBP are incubated with $10^6$ cells (SCC4, SCC9, SCC15, SCC25, HTB126, HTB127, PC-3 and LNCaP) in media for a 1 hr at 37° C. The cells are then washed 3 times with TBS-Tween and the HBP stained with FITC-anti-M13 antibodies and analyzed by flow cytometry. These studies reveal that non-permeabilized tumor cell lines (SCC4, SCC9, SCC15, SCC25, HTB126, and PC-3) possess varying levels of M13 phage staining on their cell surfaces. Furthermore, if the cells are permeabilzed prior to the addition of antibody, then cell surface staining coupled with internalized phage reveals enhanced staining. However, GMSM-K, an established epithelial cell line, treated in a like manner, reveals little or no staining. Results similar to those obtained for GMSM-K cells are also obtained for HTB125 and PZ-HPV normal breast and prostate cell lines respectively.

B. Immunoprecipitation Analysis: To verify the association of M13-binding phage with specific cell lines SCC4 and GMSM-K cells are treated with an HBP for 1 hr, then washed 3 times with TBS-Tween and the plasma membranes are isolated and immunoprecipitated with anti-M13 antibodies. This results in two protein bands one band with a Mr=47k and another band with a Mr-27k. The 47k band is identified as Hsp47 by Western blot analysis.

C. Immunofluorescence and Confocal Microscopy:

1. Immunofluorescence and confocal microscopy:

Immunofluorescence microscopy is carried out as described above. To visualize cell surface Hsp47 or M13 bacteriophage, the cells are not permeabliized but treated and fixed with 1-% paraformaldehyde as described for cytometric analyses. However, to prevent non-specific binding, the cells are blocked with 10% pig serum in PBS for 1 hr. The cells are then incubated with anti-Hsp47 or anti-M13 bacteriophage antibodies (Amersham Pharmacia-Biotech, Piscataway, N.J.), washed with PBS, and incubated for 1 h with goat anti-rabbit IgG conjugated with either fluorescein or Texas red. Coverslips are mounted in mounting media containing an antibleaching agent (Kirkegaard & Perry Laboratories, Inc.; Gaithersburg, Md.). Cells are examined under a Zeiss II photomicroscope equipped with epifluorescence. Cells untreated with primary antibodies are used as negative controls.

Confocal images are collected using a Zeiss LSM410 confocal microscope. A FT of 488/568 with a barrier filter of 590 is used to detect Texas red staining and a FT of 560 with a barrier at 515-540 is used to generate fluorescein labeled images. Digital images are collected on a ZIP drive and figures generated using Adobe Photoshop 3.0 software (Adobe Systems Inc. Mountain View, Calif.). No fluorescence is associated with cells after incubation with secondary antibodies alone.

Confocal microscopy shows the fate and co-localization of HBP. These studies reveal that when tumor cell lines are treated with HBP, there is a distribution of staining at the cell surface, in microvesicles, and an intense staining in a perinuclear region that is coincident with the ER. Cells are then treated with M13 bacteriophage followed by double staining with Texas red-anti-Hsp47 antibodies and FITC-M13 antibodies. The localization of Hsp47 is similar to that of M13 phage staining and co-localization of antibodies reveals superimposition, yellow hues, of both M13 staining and Hsp47 staining patterns.

2. Lysosomes and the ER

To label the lysosomal compartment, cells are incubated with 1 mg/ml lysine-fixable FITC-dextran (Molecular Probes; Eugene, Oreg.) in growth medium for 4 th at 37° C. in 5% $CO_2$. After washing, cells are incubated an additional 30 min to chase the dextran from the early endosomal to the lysosomal compartments. For identification of the early and recycling endosomal compartments, cells are incubated in serum-free medium containing 50 µg/ml FITC-transferrin (Molecular Probes; Eugene, Oreg.) for 30 min at 37° C. in 5% $CO_2$. After treatments to identify the specific subcellular compartments, cells are fixed and processed for immunofluorescence and/or confocal microscopy.

Cells are cultured in the presence of FITC-conjugated dextran, followed by a chase period of 30 min to remove the dextran from early endosomal compartments, before fixation and immunostaining with the Texas red conjugated anti-M13 antibodies. SSC4 cells, which are representative of the other cell lines, demonstrates a clear identification of FITC-dextran to vesicular structures, however, the HBP staining is primarily limited to punctate vesicles in the cytoplasm and a perinuclear zone. To verify that HBP is not significantly targeted to lysosomes, SCC4 cells are fed latex beads and HBP and then fixed and processed by for immunofluorescence using anti-M 13 antibodies. In SCC4 cells, M13 signal cannot be located at the periphery of the bead, suggesting that there is minimal association with the phagosomes.

To label endosomes, SCC4 and GMSM-K cells are cultured in the presence of FITC-conjugated or Texas red-conjugated transferrin before fixation and staining with anti-M 13 antibodies. Analysis by confocal microscopy indicates that transferrin stains both the plasma membrane (ring staining at the edge of cells) and recycling endosomes (subcellular punctate staining). A very similar and overlapping pattern is observed for M13 antibody staining, consequently superimposition of the two images indicates colocalization (yellow hues) of the two signals at the punctate subcellular region and plasma membrane. Noteworthy is that GMSM-K cells provide like patterns of staining with conjugated dextran and transferrin but are not stained by anti-M13 antibodies.

D. Subcellular Fractionation

Plasma membranes are fractionated as described above.

The membrane fractions are characterized by the distribution of 5'-nucleosidase activity, a marker of plasma membrane. Plasma membranes are directly subjected to PAGE and Western analysis. For Western blots, proteins run on SDS-PAGE are immediately electrotransferred to nitrocellulose paper and blocked with 10% non-fat dry milk (NFDM). Antiserum or perimmune serum is diluted 1:2000 in the same buffer and incubated with gentle shaking overnight. The nitrocellulose is then rinsed three times for 5 min. in TBS/Tween. Antibodies to Hsp47 and M13 bacteriophage are detected with [$^{125}$I]-labeled protein A (New England Nuclear, Boston, Mass.) or Western blot analysis.

E. Peptide Synthesis

Setapeptides and dodecapeptides are prepared by continues flow solid-phase synthesis and analyzed by high-pressure liquid chromatography and mass spectrophotometry as described in previously (Cwirla et al., ibid).

Example 7

Determination of the Efficacy of Hsp47-Binding Peptides and Hsp47 Monocolonal Antibodies in Homing Chemotherapeutic Drugs to Tumor Sites in Oral Squamous Carcinoma Xenografts A. Effect of Doxorubicin Conjugated Hsp47 Tumor-Homingpeptides and Hsp47 Monoclonal Antibodies on Tumor Progression: Doxorubicin is used as a model compound to show that the homing of drug to cell surface Hsp47 in well-differentiated tumors effectively reduces the dose of drug required for a tumor response, or increases the effectiveness of drug on the chemotherpeutic index in a human oral squamous cell carcinoma xenograft model.

B. Hsp47 monoclonal antibody doxorubicin conjugates: Doxorubicin immunocongujates are formulated using a malonate linker. In essence, monoclonal antibody is conjugated to BAMME-CH DMB linker in 0.5 M borate buffer in the presence of dimethylformamide. After chromatographic purification, the functional antibody is deblocked by the addition of 100 mM carbohydrazide and purified chromatographically. Finally, the deblocked functional antibody is reacted with 10-mM doxorubicin and purified chromatographically. Similar immunoconjugates have been shown to maintain the immunoreactivity of the antibody and to have equivalent potency to unconjugated free doxorubicin without manifesting toxicity as measured by weight loss and deaths in a nude mouse xenograft mode.

C. Hsp47 binding protein doxorubicin conjugates: 1Hsp47 peptides are synthesized by the UM Biopolymer Laboratory Core Laboratory and purified by high-performance liquid chromatography. The peptides are conjugated to doxorubicin (Aldrich) with 10-ethyl-3-(3-dimethyl-aminopropyl)carbodimide hydrochloride (EDC, Sigma) and N-hydroxysuccinimide (NHS, Sigma). The conjugates are then freed of reactants by gel filtration on Sephadex G25. The presence of free drug is monitored by HPLC and nuclear magnetic resonance to be <5% of the preparation.

D. Pharmacokinetics of doxorubicin distribution as free drug, peptide conjugate, and monoclonal antibody conjugate:

1. Animals and Drug Administration: Specific-pathogen-free, adult mice (5-6 weeks of age) are maintained under conventional housing conditions. Intravenous bolus doses of drug, free doxorubicin, peptide-conjugate doxorubicin, and monoclonal antibody conjugated doxorubicin, are administered through a lateral tail vein.

2. Sampling: Blood is sampled at 5, 10, 15, 30, 45, 60, 90, 120, 180, 240, 360, 480, 960, and 1440 min after dosing. In addition, hearts, lungs, livers, kidneys, spleens, skeletal muscles, and tumors are collected at the same times notes for blood samples. In each study, blood and tissues from mice killed 5 min after delivery of vehicle serve as controls. Blood is collected by cardiac puncture into heparinized syringes, transferred to Eppendorf microcentrifuge tubes and stored on ice until centrifuged at 13,000×g for 5 min to obtain plasma. Tissues are rapidly dissected, kept on ice until weighed, and then snap frozen in liquid nitrogen. Plasma, tissues, and dosing solutions are stored frozen at −70° C. until analysis.

3. Analysis of Doxorubicin: Plasma and tissue concentrations of doxorubicin are determined by high performance liquid chromatography (HPLC). Plasma samples are extracted by conventional procedures. Two hundred μl samples of plasma are mixed with internal standard (4'-epidoxorubicin) and then mixed vigorously with 0.6 ml of chloroform/2-propanol (1:1, v/v) for 15 sec. Ammonium Sulfate (approximately 0.5 g) is added to the resulting gel and mixed thoroughly. The triphasic mixture is centrifuged for 15 min at 13,000×g. The resulting upper phase is transferred to a conical test tube and dried unde a $N_2$ jet. The dried residue is redissolved in 100 μl of mobile phase, transferred to autosampler vials, and 75 μl is injected into the HPLC system described below.

Tissue samples are thawed, immediately transferred to 17×100 mm polypropylene tubes that are held in an ice bath, and homogenized using a Polytron (Brinkman Instruments, Westbury, N.Y.), in parts (weight to volume) of phosphate-buffered saline (1.2 mM $KH_2PO_4$, 2.9 mM $Na_2HPO_4$, 154 mM NaCl, pH 7.4, Biofluids, Inc., Rockville, Md.). One part of each homogenate is then mixed with internal standard, extracted with chloroform/2-propanol, and prepared for injection into the HPLC system.

The HPLC system used includes a Hewlett-Packard (Palo Alto, Calif.) model 1100 autosampler and a Waters (Milford, Mass.) M45 pump. The column employed is an ALLTECH (Deerfield, Ill.) 10 μm $C_{18}$ Econosil column (250 length, 4.6 mm i.d.). The mobile phase consists of acetonitrile: 0.32 M ortho-phosphoric acid (27:43, v/v) and is pumped at 1 ml/min. Column eluent is monitored with an Aminco fluoromonitor set at excitation wavelength of 470 nm and emission wavelength >500 nm. With this method, good separation of doxorubicin, doxorubicinol, and internal standard is achieved, with retention times of 12.5, 7, and 15 min, respectively. The lower limit of quantitation is 0.1 nm. The detector signal is processed with a Hewlett-Packard 3392A integrator so as to integrate the area under each peak. Doxorubicin concentration in each sample is calculated by determining the ratio of doxorubicin peak area to that of the corresponding internal standard peak and comparing that ratio to a concomitantly performed standard curve prepared in the appropriate matrix.

4. Pharmacokinetic Analysis: Time courses of plasma concentrations of doxorubicin verses time are analyzed by both non-compartmental and compartmental methods. Area under the curve from zero to infinty (AUC) and terminal half-life ($t_{1/2}$) are estimated by non-compartmental analysis with the LaGrange function as implemented by the LAGRAN computer program. $CL_{tb}$ is calculated from the definition:

$$CL_{TB} = Dose/AUC$$

and steady-state volume of distribution ($V_{DSS}$) is calculated from the formula:

$$V_{DSS}Cl_{tb}/kel.$$

In addition, individual concentrations of doxorubicin in plasma versus time are fit to comparmental models with the program ADAPT II, which uses a Nelder Mead simplex as the algorithm. Two- and three-compartment, open, linear models are fit to the data. Model discrimination is based on Akaike's Information Criteria (AIC), defined as:

$$AIC = 2p + n(\ln WSSR),$$

where p represents the number of parameters in the model, n equals the number of observations, and WSSR represents the weighted sum of squares residuals.

E. Treatment of mice bearing tumors with Hsp47 homing drugs: Mice with size-matched tumors (~1 $cm^3$) are randomized into six treatment groups of no less than six animals per group: vehicle only, free doxorubicin, doxorubicin-Hsp47 binding peptide, doxorubicin-control nonbinding peptide, doxorubicin-monoclonal conjugate, Hsp47 monoclonal antibody. Power analyses indicate that at least 6 animals per group are required to see a 30% difference in survival. Generally, doxorubicin dosage in nude mice with human xenographs is 50 to 200 μg/week). Since he homing of drug to tumor is more effective than free drug, initial studies are performed with dosages of 5, 10 and 15 μg/week. The concentration of doxorubicin as equivalents is adjusted by measuring the absorbency of drug and conjugates at 490 nm and a calibration curve established to ascertain equivalents for peptide and monoclonal conjugates. The fraction of surviving animals is determined over a course of 40 days and plotted as a Kaplan-Meier survival curve. Survival is determined by examining animals daily to determine mortality. Next, a dose escalating experiment is performed in which mice are treated with doxorubicin-Hsp47 binding peptide and doxorubicin-conjugated Hsp47 monoclonal antibodies at a dose of 30 μg of doxorubicin equivalent every 21 days for 84 days. A Kaplan-Meier survival curve is constructed. In addition, following necropsy, the primary tumor weight and size are ascertained, and the presence of lymph node and pulmonary metastasis is determined. Lymph node weight and lung weight are also measured as a gross measure of metastasis supported by histological assessment.

To assess toxicity, drug dosage is escalated to 200 μg of doxorubicin-equivalent per mouse. Mice receiving elevated doses of drug receive a single dose of free doxorubicin, doxorubicin-Hsp47 binding peptide, or doxorubicin-Hsp47 monoclonal antibody. Animals are then followed for 14 days and the mean fraction of animals depicted in a Kaplan-Meier survival curve.

Animals treated with tumor homing doxorubicin-conjugates survive longer an at lower equivalent doses of drug than animals receiving free drug. In addition, along with a greater survival is a reduction in tumor size as weight, and lymph node and drug metastasis. If unconjugated Hsp47 monoclonal antibody itself has an immunotherapeutic effect in mediating a response against tumor, this is evident only in the C57BL model, as immunodeficient nude mice do not respond in such a manner and the use of unconjugated controls.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and in the figures are hereby incorporated by reference.

APPENDIX I

BINDING MOTIFS OF *CPB2* A POTENTIAL CELL SURFACE TARGET FOR CARCINOMA CELLS

Previously we have shown (*J. Cellular Biochem., 1999*) that among many cell lines the *CPB2* gene product, Hsp47, eludes its retention receptor, *erd2P*, resulting in the appearance of Hsp47 on the cell surface associated with the tetraspanin protein CD9. In that Hsp47 possesses a highly restricted binding cleft, random peptide display libraries were used to characterize peptides binding to Hsp47 and then to target this protein on carcinoma cell lines in vitro. Comparison of the clones obtained from panning revealed little specific homology based on sequence alone. To determine whether carcinoma cells expressing Hsp47 could selectively take up the selected bacteriophages, traditional immunofluorescence and confocal microscopy were employed. These studies revealed that phage-displaying Hsp47 binding peptides bound to cell lines expressing Hsp47 and that the peptides were rapidly taken up to a location coincident with Hsp47 staining. These observations were confirmed by cytometric analyses. These data indicate that *CBP2* product may provide a molecular target for chemotherapy and/or imaging of malignancies.

*Abbreviations:* *CPB2*, collagen binding protein 2; ER, endoplasmic reticulum; ATCC, American Type Culture Collection; TBS, Tris buffered saline; PBS, phosphate buffered saline; PEG, polyethylene glycol, FITC, fluoresceinistothiocyanate.

There is an on going quest to identify specific cell surface targets by which to direct treatment or to image neoplastic cells. For example, one group of proteins that has been used as targets for drug delivery is chimeric molecules created by cancer-associated chromosomal abnormalities. However, such molecules are usually unique to a particular tumor (Baron et al., 1997; Diez de Medina SG et al., 1997). In addition to the aforementioned proteins, potential sources of such targets are the products of genes that are amplified at a particular chromosome locus in malignancy. For example the chromosome locus 11q13–14 is commonly amplified in human cancers that include cancers of the head and neck, lung, esophagus, bladder and breast (Schuuring et al., 1992). This amplicon is large, spanning 2.5-5 Mb and harbors several genes with known oncogenic potential (Bekri, 1997). In breast cancer, this locus is amplified in ~13% of primary tumors while in head and neck cancers amplification may represent 40%-76% of tumors. A more detailed map of this region has evolved indicating that as many as five distinct amplification units exist on 11q13. Among these units is a genomic area encompassing the GARP gene at 11q13.5–q14.1. Assessment of this region, located telomeric to *CCDN1* and *EMS1,* has revealed a number of genes in the regional map, namely *CBP2 (Hsp47)* and *"spot 14"* at chromosome locus 11q13.5 with, *CLNS1A, UVRAG,* and *PAK1* located telomeric to this later region. Thus, narrowing the core of the 11q13–q14 amplicon to a 350-kb area encompassing D11S533 on its telomeric side (Bekri, 1997; Moncur, 1998).

In assessing this amplicon it became evident that the gene product of

*CBP2* was associated with, and may distinguish a group of malignant tumors (Morino et al., 1997; Morino et al., 1995; Morino et al., 1994; Shirakami et al., 1995a; Shirakami et al., 1995b; Shirakami et al., 1995), as well as, being localized to extravillous cytotrophoblasts and decidual cells at the fetal maternal interface (Pak et al., 1997; Shirakami et al., 1995b; Morino et al., 1995; Morino et al., 1994; Morino et al., 1997; Shirakami et al., 1995). Interestingly, *CBP2,* mapped to chromosome 11q13.5, shares a locus with *Spot 14* a key gene expressed in lipogenic neoplasms (Moncur, 1998).

Normally, the *CBP2* gene product, Hsp47, is limited to the ER-Golgi where it is first associated with procollagen chains at a very early point during translation of nascent chains (Sauk et al., 1994). Hsp47 is retained within these cellular compartments by recycling of the erd2 gene product, KDEL receptor, that associates with the COOH-terminus sequence RDEL of Hsp47 (Sauk et al., 1997). However, in some tumors Hsp47 is expressed independent of its chaperone properties and eludes or leaks from this surveillance mechanism and manifests on the cell surface, but is not secreted into the medium. Although previous studies have demonstrated that Hsps such as gp96 are tightly surface-bound peripheral membrane proteins, the precise mechanism of anchorage was unclear, albeit ionic interactions with other proteins could be excluded (Tamura Y, 1997). Hsp47, like gp96, lacks sequence characteristics for farnesylation, palmitation, isoprenyllation or myristylation; consequently covalent bonding also appears to be an unlikely anchoring mechanism (Tamura Y, 1997; Altmeyer et al., 1996; Tamura Y, 1997). Interestingly, Hsp47 has been shown to associates with the tetraspanin protein CD9 in some epidermoid carcinoma cell lines (Hebert et al., 1999). Moreover, in these instances Hsp47 has been shown to be easily recovered, even without the use of cross-linking, from membrane immunoprecipitates utilizing anti-CD9 antibodies, suggesting the presence of hydrophobic interactions between these proteins (Hebert et al., 1999).

Hsp47 unlike many other chaperones has been shown to possess a limited number of intracellular ligands (Nakai et al., 1989). Although previous studies have defined the Hsp47 binding to a region defined by the anti-propeptide antibody SP1.D8 (Hu et al., 1995), to a region of procollagen to N-propeptides of the $\alpha 1(I)$-chains between residues 23-151, and to gelatin (Nagata et al., 1988), specific peptide motifs have yet to be determined for this binding (Hu et al., 1995).

Here, we report on a repertoire of bacteriophage-peptides obtained from panning experiments with Hsp47. Colocalization of some of these peptides with Hsp47 in a number of tumor cell lines demonstrates that the peptides can be directed to an intracellular location spatially coincident with Hsp47. These results indicate that cell surface Hsp47 is not permanently anchored to the cell surface and that this protein undergoes recycling with an intracellular pool. In addition, these studies suggest that expression of the *CBP2* in tumors may provide a target for phage directed gene therapy, a mechanisms by which to deliver drugs, or a means of imaging occult disease and metastases.

MATERIAL & METHODS

*Cell Lines:* Studies were performed using a number of established cell lines of human oral squamous cell carcinomas [SCC4, SCC9, SCC15, and SCC25] were obtained from ATCC, and a transformed normal oral keratinocyte cell line GMSM-K was courtesy of Dr. V. Murrah (UNC, Chapel Hill, NC). Breast carcinomas [HTB126, HTB127], and HTB125 normal breast cells were likewise obtained from ATCC. In addition, prostate cell lines PC-3, LNCaP, and PZ-HPV were courtesy of Dr. R. Franklin (UM, Baltimore, MD). In the studies presented here, cells were cultured in a 1:1 mixture of Ham's F12 and Dulbecco's modified Eagle's medium containing 10% fetal calf serum, hydrocortisone (0.4µg/ml, Sigma) at 37°C in a 5% $CO_2$ air atmosphere. For breast carcinoma cell lines 10 µg/ml of insulin was added to the medium as prescribed by ATCC and PZ-HPV cells were grown in KSF medium. Cells were subcultured by dissaggregation with trypsin (0.1%)-EDTA (0.01%) in phosphate buffered saline [PBS] at pH 7.5.

*Antibodies:* The monoclonal antibody SPA-470 to Hsp47 (StressGen, Victoria, BC) was used, as well as, a Hsp47 rabbit polyclonal antibody prepared against a 22-mer peptide corresponding to the N-terminal sequence of mouse Hsp47 that was conjugated to Keyhole Limpet hemocyanin (Sauk et al., 1994). The anti-M13 monoclonal antibody was procured from Amersham Pharmacia Biotech (Piscataway, NJ). Monoclonal antibodies for cytometric analyses were directly conjugated with fluorescein using 5(6) carboxyfluorescein-N-hydroxy succinimide ester kit (Boehringer Mannheim, Indianapolis, IN) or labeled with SA-Red670™ following biotinylation of the antibody using EZ-Link™ Sulfo-NHS-LC-Biotinylation kit (Pierce, Rockville, Ill).

*Affinity Panning of a Library of Peptides:* To study the binding specificity of Hsp47, we utilized two bacteriophage libraries with random septapeptide Ph.D.-7, New England Biolabs; Beverly, MA) or dodecapeptide (Ph.D.-12, New England Biolabs; Beverly, MA) inserts at the N-terminus of pIII protein. The Ph.D.-7 library consists of ~2.8 x $10^9$ electroporated sequences amplified once to yield ~ 70 copies of each sequence in 10µl of supplied phage. The Ph.D.-12 library consisted of ~2.7 x $10^9$ electroporated sequences amplified once to yield ~55 copies/10 µl of supplied phage.

*Selection of Hsp47-Binding Bacteriophages by Affinity Panning:*

Bacteriophages displaying peptides recognized by Hsp47 were identified using the Ph.D.-7 or Ph.D.-12 kits (New England Biolabs; Beverly, MA) and the protocols modified for a biotinylated target. In essence, 96 wells of a microtitration plate were coated with 15 µl of streptavidin (1mg/ml) in 135 µl of 0.1M $NaHCO_3$ pH 8.6, with gentle agitation in a humidified chamber overnight at 4°C. After removal of the streptavidin solution the wells were washed three times with TBS containing 0.05% Tween 20 (TBS-Tween) and then blocked by incubation for 1 hr at 37°C with 1% BSP in PBS containing 0.1 µg/ml streptavidin.

Next, phage was precomplexed with biotinylated Hsp47 by adding 0.1 µg biotinylated Hsp47 and 2 x $10^{11}$ pfu of the input phage in 400 µl TBS-Tween and incubated for 60 min. The phage-target complex solution was then added to the washed blocked plates and incubated at room temperature for 10 min. Biotin was added to a final concentration of 0.1 mM and incubated for 5 min. to displace streptavidin-binding phage. Non-binding phage were discarded and the plates washed 10 x with TBS-Tween (0.1%). The wells were then treated with 15 µl of 1 M Tris-HCl; pH 2.2, containing 1 mg/ml BSA for 5 minutes to elute Hsp47-phage. The samples were neutralized with 1 M Tris-HCl; pH 9.1, and amplified by adding to 20 ml of ER 2537 culture incubated at 37°C with vigorous shaking for 4.5 hrs. The cultures were then transferred to fresh tubes centrifuged at 10,000 rpm, 4°C, for 10 mins. The supernatants were transferred to fresh tubes and phage precipitated with 1/6 volume of PEG/NaCl at 4°C, overnight. To 4 ml of LB media a single colony of ER2537 was inoculated and then incubated at 37°C with vigorous shaking until the culture reached mid-log phase ($O.D._{600}$ ~0.5). A pellet was obtained by centrifugation for 15 min at 10,000 rpm, 4°C. The pellet was suspended in 1 ml of TBS and centrifuged for 5 min, 10,000 rpm, 4°C. The supernatant was transferred to a fresh tube and precipitated with 1/6 volume of PEG/NaCl on ice for 1 hr. Following centrifugation the pellet was resuspended in 200 µl TBS. The eluate was titered and plated onto LB/IPTG/XGal plates and incubated overnight. Since the library phage are derived from the common cloning vector M13mp19, which carries the *lacZα* gene, phage plaques appear blue when plated on media containing Xgal and IPTG. Blue colonies were selected for sequencing or used for a second round of panning. As a control streptavidin was used as a target and after three round of panning a to verify a consensus sequence for streptavidin-binding peptides.

Screening for Hsp47-Binding Bacteriophages:

Clones of blue colonies from plates containing 50-200 colonies were transferred to nitrocellulose filters. The bacteria were washed from the filters with PBS containing 0.05% Tween 20 and 1% bovine serum albumin, and the filters were then incubated for 30 min in the same buffer before washing three times with PBS-Tween. Following incubation for 1hr in 5 ml of biotinylated Hsp47 (0.1-2µg/ml in PBS-Tween), the filters were again washed three times in PBS-Tween. The positions of the clones that had secreted Hsp47-binding bacteriophages were then located by one of two methods: the filters were incubated with 5 ml of alkaline phosphatase-conjugated streptavidin (1/10,000 dilution in PBS-Tween; Pierce, Rockford, IL) for 1 hr at room temperature before extensive washing with PBS-Tween, or the filters were incubated for 1 hr in 5 ml of an anti-biotin antibody (1/50,000 dilution in PBS-Tween; Pierce, Rockford, IL), washed, and incubated with a rabbit anti-goat immunoglobulin antibody conjugated to alkaline phosphatase (1/5,000 dilution in PBS-Tween; Pierce, Rockford, IL). In each case, alkaline phosphatase activity was revealed using a mixture of nitroblue tetrazolium/and 5 bromo-4-chloro-3-indolylphosphate tolidium (Bethesda Research Labs, Rockville, MD) as substrate.

Determination of the Sequence of Bacteriophage-Displayed Peptides:

Single-stranded bacteriophage DNAs were purified and sequenced as -96 primer an oligonucleotide (5'-CCCTCATAGTTAGCGTAACG-3'). Sequencing reactions were carried out using an ABI Prism Model 373 Version 3.0.

Program to Score Hsp47-Binding Peptides:

To characterize peptides that bind to Hsp47 we compared the starting and selected libraries in a position-dependent manner. A statistical analysis was performed by maximum likelihood and bootstrap resampling. This revealed the distribution of residues by position in Hsp47-binding peptides compared to peptides in the original library. To codify the preferences obtained above we used a scoring system previously described for BiP (Cwirla et al., 1990) that would be used to predict Hsp47-binding sites in synthetic and naturally occurring polypeptides. In so doing a score is given to each of the possible 20 amino acids at each position of the seven-residue core sequence. These scores were derived from the fold difference in the overall abundance of each residue in the peptides displayed by the selected and nonselected bacteriophage populations. The scoring for each of the seven residue sequences present in each septapeptide was determined as previously described (Cwirla et al., 1990).

To validate our scoring set of Hsp47-binding sequences, a second set of Hsp47-binding sequences not part of the database used to generate the scoring matrix is necessary. To accomplish this a second library consisting of independent recombinant bacteriophages displaying random dodecapeptides was used (Ph.D-12, New England Biolabs, Beverly, MA). Sequences were then compared by position specific iterated BLAST, pattern Hit Initiated BLAST, and BLAST 2 sequences against each other (NCBI). In addition, the hydropathic profiles of two peptides were compared using the Weizmann Institute of Sciences Genome and Bioinformatics database.

Peptide Synthesis:

Setapeptides and dodecapeptides were prepared by continuos flow solid-phase synthesis and analyzed by high-pressure liquid chromatography and mass spectrophotometry as described in previously (Cwirla et al., 1990).

Cytometric Analyses:

Cells grown *in vitro*, as described above, were washed and incubated in a 0.5% solution of Polyglobin N to block unsaturated Fc receptors and reduce non-specific binding of monoclonal antibodies (Takeshita et al., 1995). Next, 50 ml of the cell suspension ($1 \times 10^6$ cell/ml) was incubated with 2.5 ml (1mg) of antibodies, conjugated with fluorescein, or SA-Red670™ (GibcoBRL, Gaithersburg, MD). After washing, the cell pellet was resuspended in PBS containing BSA for flow cytometric assay. To assess intracellular Hsp47 and M13 bacteriophage, cells were first permeabilized with 0.1% Saponin as previously described (Tang et al., 1994; Tang et al., 1993). Samples were then analyzed on a FACScan flow cytometer (Becton Dickinson, San José, CA). The 488 nm Argon laser was run at 15 nW of power. The data from fluorescein conjugates were collected after a 530/30 BP filter. For two-color flow cytometric analysis either fluorescein or Red670™ were employed with propidium iodide. The filters used were 600 nm dichroic SP; 525 ± 15nm BP (fluorescein) and 645 LP (Red670™).

Propidium iodide was used to assess cell cycle and stain for dead cells. For these studies a hypotonic citrate solution containing PI was added to ~ $1 \times 10^6$ washed cells to a concentration of 1mM. Cells were labeled for 20 minutes, then analyzed on the FACScan in their staining solution. Orange PI fluorescence was collected after a 585/42 nm BP filter.

Electronic compensation was used among fluorescence channels collecting emissions to remove residual spectral overlap. Fluorescence data were displayed on a four-decade long scale. A minimum of 10,000 events was collected on each sample. Analysis of the data was performed with LYSYS II software (Becton Dickinson, Mansfield, MA). Fluorescence dual parameter contour plots were used for exclusion of debris and clumps. This method of gating allowed ready discrimination of debris from dead cells (low forward light scatter and high PI fluorescence).

*Immunofluorescence and Confocal Microscopy:* Immunofluorescence microscopy was carried out after the method of Tang et al, (Tang et al., 1994; Tang et al., 1993). To visualize cell surface Hsp47 or M13 bacteriophage, the cells were not permeabilized but treated and fixed with 1-% paraformaldehyde as described for cytometric analyses. However, to prevent non-specific binding, the cells were blocked with 10% pig serum in PBS for 1 hr. The cells were then incubated with anti-Hsp47 or anti-M13 bacteriophage antibodies (Amersham Pharmacia-Biotech, Piscataway, NJ), washed with PBS, and incubated for 1 h with goat anti-rabbit IgG conjugated with either fluorescein or Texas red. Coverslips were mounted in mounting media containing an antibleaching agent (Kirkegaard & Perry Laboratories, Inc.; Gaithersburg, MD). Cells were examined under a Zeiss II photomicroscope equipped with epifluorescence. Cells untreated with primary antibodies were used as negative controls.

Confocal images were collected using a Zeiss LSM410 confocal microscope. A FT of 488/568 with a barrier filter of 590 was used to detect Texas red staining and a FT of 560 with a barrier at 515-540 were used to generate fluorescein labeled images. Digital images were collected on a ZIP drive and figures generated using Adobe Photoshop 3.0 software (Adobe Systems Inc. Mountain View, CA). No fluorescence was associated with cells after incubation with secondary antibodies alone.

To label the lysosomal compartment, cells were incubated with 1mg/ml lysine-fixable FITC-dextran (Molecular Probes; Eugene, OR) in growth medium for 4h at 37°C in 5% $CO_2$. After washing, cells were incubated an additional 30 min to chase the dextran from the early endosomal to the lysosomal compartments. For identification of the early and recycling endosomal compartments, cells were incubated in serum-free medium containing 50 µg/ml FITC-transferrin (Molecular Probes; Eugene, OR) for 30 min at 37°C in 5% $CO_2$. After treatments to identify the specific subcellular compartments, cells were fixed and processed for immunofluorescence and/or confocal microscopy.

Subcellular Fractionation of Plasma Membranes: The method for fractionating plasma membranes was modified after the methods described by Weber et al. (Weber TM et al., 1988). The samples were treated with bacterial collagenase to eliminate the possibility of cytoplasmic derived procollagen-Hsp47 binding to the cell surface integrin receptors as a result of cell fractionation. The initial supernatant was centrifuged in a Sorvall SS34 rotor at 48,000 $g$ at 4°C for 15 min. and the high-density microsome pellet was resuspended in 40µl of buffer. The supernatant was further centrifuged in a Beckman 70.1 rotor at 300,000 $g$ at 4°C for 75 min. and the low-density microsome pellet was resuspended in 60 µl of buffer.

The membrane fractions were characterized by the distribution of 5'-nucleosidase activity, a marker of plasma membrane (Avruch and Wallach, 1971). Plasma membranes were directly subjected to PAGE and Western analysis. For Western blots, proteins run on SDS-PAGE were immediately electrotransferred to nitrocellulose paper and blocked with 10% non-fat dry milk (NFDM). Antiserum or perimmune serum was diluted 1:2000 in the same buffer and incubated with gentle shaking overnight. The nitrocellulose was then rinsed three times for 5 min. in TBS/Tween. Antibodies to Hsp47 and M13 bacteriophage were detected with [$^{125}$I]-labeled protein A (New England Nuclear, Boston, Mass) or Western blot analysis as described previously (Sauk et al., 1997)

RESULTS

To elucidate the binding motifs of Hsp47, we utilized two bacteriophage libraries with random septapeptide or dodecapeptide inserts at the N-terminus of pIII protein. Because peptides containing at least seven or eight residues are generally required for efficient binding we first chose a library of bacteriophages that displayed septameric peptides (Ph.D.-7, New England Biolabs; Beverly, MA). To begin to characterize these peptides, 70 individual bacteriophage clones were picked at random from the unselected library, and the amino acid sequences of the variable septapeptide inserts were deduced from the nucleotide sequences of the corresponding coding region. All amino acids are represented, although their frequencies do not always correspond to those expected from the relative numbers of codons encoding each residue.

The sequences of septapeptides displayed by 54 Hsp47-binding bacteriophages obtained by panning were determined by DNA sequence analysis of the corresponding region of the bacteriophage genome. The peptide sequences from the 54 clones that bound Hsp47 were first considered as a single population and compared with those from the 70 clones picked randomly from the starting library. Tabulation of the hydrophilicities of the Hsp47-binding bacteriophages revealed that two general populations of peptides that were selected by panning. One group of peptides was represented by hydrophilic peptides and the other by a smaller hydrophobic group of peptides (Figure 1).

Comparison of the overall amino acid composition of the two populations, selected and unselected, of septapeptides revealed that asparagine (N), threonine (T), tyrosine (Y) and proline (P) were particularly enriched, while phenylalanine (F), aspartic acid (D), and arginine (R) were significantly depleted (Figure 2a, 2b). However, when considered individually, the hydrophobic group of peptides was noticeably enriched in tryptophan, and leucine as well as valine and alanine.

The five-residue spacer linking the variable septapeptides to the mature pIII protein contained no enriched residues. Thus, indicating that the spacer residues are unlikely to contribute to the binding activity of selected bacteriophages, allowing us to look only within the variable septapeptide sequences for the presence of a binding motif. Inspection of the selected hydrophobic peptides revealed that a residue motif best described as XHyHyXXXHyHy, where Hy is a large hydrophobic amino acid (usually W,L, or F) and X is any amino acid. This core motif is also identified in selected residue from a Ph.D-12 library represented by a motif XHyHyXXHyXXXXHyHy. Taken together these data suggest that the peptide-binding site contain a deep hydrophobic pocket separated by charged hydrophilic residues (Figure 3). The peptide motif described as XXHyHyXXX best described the selected hydrophilic peptides selected from the library. Interestingly, a similar core motif (HyXXXHyHyXXHyXXX) could also be identified in selected resides from the dodecapeptide library. However, a small number of peptides were completely lacking in hydrophobic residues although they were selected during panning of Hsp47.

Recognizing that procollagen I was a natural ligand for Hsp47, BLAST program analyses were performed to assess the sequence homology between bacteriophage-displayed peptides and procollagen I and the selected dodecapeptides. Interestingly, little specific homology was observed based on sequence alone. However, when the hydropathic profile of procollagen I (1) was compared with the dodecapeptides obtained from three rounds of panning, using Kyte-Doolittle method of calculating hydrophilicity over a window length of 7, all of the phage displayed peptides were represented by specific regions within the procollagen molecule. Interestingly, most of the hydrophobic peptides were localized to regions within the N-propeptide region (residues 59-71) or the C-propeptide region (residues 1344-1445). Conversely, the most of the hydrophilic peptides were localized the regions with the helical region of procollagen (residues: 283-295, 470-482, 666-678, 727-739, 1040-1052, and 1087-1099) with only one peptide localized to a sequence within the N-propeptide region (residues 100-112) (figure 4).

To gain insight into the subcellular localization of Hsp47-binding phage (HBP) on tumor cells, we incubated 25µl of HBP with $10^6$ cells (SCC4, SCC9, SCC15, SCC25, HTB126, HTB127, PC-3 and LNCaP) in media for a 1 hr at $37^{\circ C}$. The cells were then washed 3 times with TBS-Tween and the HBP stained with FITC-anti-M13 antibodies and analyzed by flow cytometry. These studies revealed that non-permeabilized tumor cell lines (SCC4, SCC9, SCC15, SCC25, HTB126, and PC-3) possessed varying levels of M13 phage staining on their cell surfaces. Furthermore, if the cells were permeabilzed prior to the addition of antibody, then cell surface staining coupled with internalized phage revealed enhanced staining. However, GMSM-K, an established epithelial cell line, treated in a like manner, revealed little or no staining. Figure 5 depicts a representative tumor cell line, SCC4 cells, compared to GMSM-K cells. Results similar to those obtained for GMSM-K cells were also obtained for HTB125 and PZ-HPV normal beast and prostate cell lines respectively.

To verify the association of M13-binding phage with specific cell lines SCC4 and GMSM-K cells were treated with an HBP for 1 hr, then washed 3 times with TBS-Tween and the plasma membranes were isolated and immunoprecipitated with anti-M13 antibodies. This resulted in two protein bands one band with a Mr=47k and another band with a Mr=27k (Figure 6). The 47k band was identified as Hsp47 by Western blot analysis.

Confocal microscopy was also employed to determine the fate and co-localization of HBP. These studies revealed that when tumor cell lines were treated with HBP that there was a distribution of staining at the cell surface, in microvesicles and an intense staining in a perinuclear region that was coincident with the ER (Hebert et al., 1999). Cells were then treated with M13 bacteriophage followed by double staining with Texas red-anti-Hsp47 antibodies and FITC-M13 antibodies. The localization of Hsp47 was similar to that of M13 phage staining and co-localization of antibodies revealed superimposition, yellow hues, of both M13 staining and Hsp47 staining patterns (Figure 7).

Next, we determined whether HBP localized to the late endosomal/lysosomal compartment. To label the lysosomal compartment, cells were cultured in the presence of FITC-conjugated dextran, followed by a chase period of 30 min to remove the dextran from early endosomal compartments, before fixation and immunostaining with the Texas red conjugated anti-M13 antibodies. SSC4 cells, which were representative of the other cell lines, demonstrated a clear identification of FITC-dextran to vesicular structures, however, the HBP staining was primarily limited to punctate vesicles in the cytoplasm and a perinuclear zone (Figure 8).To verify that HBP was not significantly targeted to lysosomes SCC4 cells were feed latex beads and HBP and then fixed and processed by for immunofluorescence using anti-M13 antibodies. In SCC4 cells, M13 signal could not be located at the periphery of the bead, suggesting that there was minimal association with the phagosomes.

Since we had previously shown that Hsp47 was expressed on the cell surface we considered whether HBP bound to cell surface Hsp47 might be present in recycling endosomes. To label these compartments SCC4 and GMSM-K cells were cultured in the presence of FITC-conjugated or Texas red-conjugated transferrin before fixation and staining with anti-M13 antibodies. Analysis by confocal microscopy indicated that transferrin stained both the plasma membrane (ring staining at the edge of cells) and recycling endosomes (subcellular punctate staining). A very similar and overlapping pattern was observed for M13 antibody staining, consequently superimposition of the two images indicated colocalization (yellow hues) of the two signals at the punctate subcellular region and plasma membrane (Figure 9). Noteworthy was that GMSM-K cells provided like patterns of staining with conjugated dextran and transferrin but were not stained by anti-M13 antibodies (not shown).

Based on the sequence of peptides isolated by panning, septapeptides and dodecapeptides consistent with the predicted models obtained from scoring were synthesized, labeled with FITC and incubated with SCC cells that were shown to bind and take-up HBP. Although none of the cell lines took up the septapeptides all of the synthesized dodecapeptides could be noted in the cytoplasm of tumor cells after 15 min. of incubation (Figure 10).

DISCUSSION:

The use of random peptide libraries has been shown to be a valuable tool for identifying novel therapeutic molecules. The libraries represent an enormous number of peptide sequences displayed either on the virion surface of filamentous phage clones or on a solid phase synthetic support. Central to this strategy is the observation that peptides isolated by affinity selection from such libraries typically interact with biologically relevant domains of the target proteins (Smith and Scott, 1993; Kitamura et al., 1992; Burkhardt et al., 1991; Smith et al., 1995; Pasqualini et al., 1996; Pasqualini and Ruoslahti, 1996; Ruoslahti, 1997; Ruoslahti, 1996; Hutchcroft et al., 1992; Borst et al., 1993). This strategy often results in a number of peptides that apparently bind to a single domain of a protein or receptor. Curiously, the peptides often lack sequence similarity and are thus reminiscent of the discovery of mimotopes (Bowditch et al., 1996; Partidos et al., 1997; Bowditch et al., 1996), where short peptides bind to the antigen-binding site of antibodies even though they differ in sequence from the antigen. Clearly, this appears to be the case here, where myriads of peptides were localized from both libraries. These peptides, however, could be divided into two groups. One group characterized by a prevalence of hydrophobic residues and a second group characterized by a preponderance of charged hydrophilic residues. The enrichment of valine and alanine as well as tryptophan and leucine in peptides displayed by this selected group of bactiophages is consistent with the affinity of Hsp47 to a region that is determined by its hydrophobic character. In addition, the demonstration of HBP binding by dodecapeptides with a motif of XXXXXHyXXHyXHyHy indicates that the hydrophobic domains of the ligand need not be located at the pIII terminus. Thus, our data suggests that these selected peptides describe a peptide binding site for Hsp47 that contains at a long pocket which can accommodate the side chains of large hydrophobic and aromatic amino acids and that contain adjacent regions that can interact with charged residues. These conclusions are supported by three-dimensional structural modeling studies which reveal that mature Hsp47 possesses a binding region as a long, deep cleft, which at physiologic pH, the base is formed by a β-sheet with sides formed by helices. The helices project hydrophobic amino acid residue side chains in toward the cleft while β-sheet project hydrophobic amino acid residue side chains up from the bottom. (Davids et al., 1995). Moreover, this model explains the ability of Hsp47 to bind to hydrophobic regions within the *N*-propeptide as described previously (Hu et al., 1995) and likewise to the backbone of denatured collagen (gelatin) (Nagata et al., 1988). Interesting, was the discovery that regions within the C-propeptide region of procollagen might also provide a binding site for Hsp47, since carboxyterminal association of procollagen chains are implied in chain assembly (Chessler, 1993b; Lees, 1997; Oliver, 1996; Lees, 1994; Chessler, 1993a).

To gain further understanding into the nature and fate of Hsp47 displayed on the cell surface of cancer cells we localized M13-phage selected from the bacteriophage libraries to the cell surface of a number of oral cancer, breast and prostate cell lines utilizing flow cytometric analyses. In so doing, we demonstrated that permeabilization of the cells prior to antibody staining enhanced the FACS signaling, suggesting that M13 was internalized into the cells. Immunoprecipitation of the plasma membranes of the tumor cells exposed to selected bacteriophages displaying Hsp47 binding peptides revealed that Hsp47 was immunoprecipitated with the M13 bacteriophage as well as another 27kD protein which may represent CD9 (Hebert et al., 1999), thus, substantiating that the selected HBP were associated with cell surface Hsp47 complexes. Confocal imaging was then employed to begin to localize the fate of the internalized selected peptide displaying bacteriophage. These studies revealed that short-term incubation resulted in selected peptides being localized to the cell surface and recycling endosomes. This was not unexpected since membrane turnover of cell surface proteins and receptors normally follow such a course. However, surprisingly only a small amount of the internalized peptides could be identified in lysosomes distinguished by FITC-dextran staining. Antithetically, when the cells were stained for both M13 displayed HBP and Hsp47 there was a concurrent localization, yellow hues, of both antibodies to coincident intracellular locations represented by recirculating endosomes and the ER.

Collectively, these data indicate that unlike cell surface peptide hormone receptors that undergo internalization by endocytosis upon binding to ligands, which are then sorted in endosomes to lysosomes where they are presumably degraded (Gruenheid, 1999). Cell surface ER proteins are routed with their ligands back to the ER with only a small amount of the ligand destined for lysosomal processing. Conceivably, the use of an ER protein with a binding capacity to a restricted number of ligands will permit targeting of drug conjugates or imaging compounds directly to tumor cells expressing these proteins. Such targeting offers the possibility of minimizing nonselective toxic effects. Moreover, one would expect that multidrug resistance would be less important in the case of cell surface ER-mediated transport of the drug across the cell membrane (Czerwinski et al., 1998). Although these *in vitro* data indicate that a cell surface expressed Hsp47 contain elements that might be able to deliver a very selective tumor agent, elements that may have importance in determining this activity have yet to be tested in this model. These elements include the type of toxic moiety which could deliver its effect in the ER and the necessary level of Hsp47 expressed on the cell surface to deliver drug and the ability to recycle for additional ligand binding and transport (Czerwinski et al., 1998). In that septapeptides displayed at the pIII terminus of bacteriophage were taken up by tumor cells while their synthetic homologues were not internalized, indicates that the use of such peptides would necessitate peptide linkers , that are stable in the circulation, capable of displaying the peptides for binding and are yet able to be processed following internalization. Ongoing research in our laboratory is directed to resolving these issues and to the application of our findings to clinically relevant tumors.

Reference List

Altmeyer, A., Maki, R.G., Feldweg, A.M., Heike, M., Protopopov, V.P., Masur, S.K., and Srivastava, P.K. (1996). Tumor-specific cell surface expression of the-KDEL containing, endoplasmic reticular heat shock protein gp96. International Journal of Cancer 69, 340-349.

Avruch, J. and Wallach, D.F. (1971). Preparation and properties of plasma membrane and endoplasmic reticulum fragments from isolated rat fat cells. Biochimica et Biophysica Acta 233, 334-347.

Baron, A.T., Huntley, B.K., Lafky, J.M., Reiter, J.L., Liebenow, J., McCormick, D.J., Ziesmer, S.C., Roche, P.C., and Maihle, N.J. (1997). Monoclonal antibodies specific for peptide epitopes of the epidermal growth factor receptor's extracellular domain. Hybridoma 16, 259-271.

Bekri, S. (1997). Detailed map of a region commonly amplified at 11q13–q14 in human breast carcinoma. Cytogenet.Cell Genet. 79, 125-131.

Borst, J., Brouns, G.S., de, V.E., Verschuren, M.C., Mason, D.Y., van, D., and JJ (1993). Antigen receptors on T and B lymphocytes: parallels in organization and function. Immunological Reviews 132, 49-84.

Bowditch, R.D., Tani, P., Fong, K.C., and McMillan, R. (1996). Characterization of autoantigenic epitopes on platelet glycoprotein IIb/IIIa using random peptide libraries. Blood 88, 4579-4584.

Burkhardt, A.L., Brunswick, M., Bolen, J.B., and Mond, J.J. (1991). Anti-immunoglobulin stimulation of B lymphocytes activates src-related protein-tyrosine kinases. Proc.Natl.Acad.Sci.U.S.A. *88*, 7410-7414.

Chessler, S.D. (1993a). BiP binds type I procollagen pro alpha chains with mutations in the carboxyl-terminal propeptide synthesized by cells from patients with osteogenesis imperfecta. J.Biol.Chem. *268*, 18226-18233.

Chessler, S.D. (1993b). Mutations in the carboxyl-terminal propeptide of the pro alpha 1(I) chain of type I collagen result in defective chain association and produce lethal osteogenesis imperfecta. J.Biol.Chem. *268*, 18218-18225.

Cwirla, S.E., Peters, E.A., Barrett, R.W., and Dower, W.J. (1990). Peptides on phage: a vast library of peptides for identifying ligands. Proceedings of the National Academy of Sciences of the United States of America *87*, 6378-6382.

Czerwinski, G. (1998). Cytotoxic agents directed to peptide hormone receptors: defining the requirements for a successful drug. Proc.Natl.Acad.Sci.U.S.A. *95*, 11520-11525.

Davids J.W., E.-T.T.S.H.N.A.N.K.M.A.D. (1995). Modeling the three-dimensional structure of serpin/molecular chaperone Hsp47. Bioorganic Chemistry *23*, 427-438.

Diez de Medina SG, Chopin, D., El, M.A., Delouvee, A., LaRochelle, W.J., Hoznek, A., Abbou, C., Aaronson, S.A., Thiery, J.P., and Radvanyi, F. (1997). Decreased expression of keratinocyte growth factor receptor in a subset of human transitional cell bladder carcinomas. Oncogene *14*, 323-330.

Gruenheid, S. (1999). The iron transport protein NRAMP2 is an integral membrane glycoprotein that colocalizes with transferrin in recycling endosomes. J.Exp.Med. *189*, 831-841.

Hebert, C., Norris, K., Della, C.R., Reynolds, M., Ordonez, J., and Sauk, J.J. (1999). Cell surface colligin/Hsp47 associates with tetraspanin protein CD9 in epidermoid carcinoma cell lines. J.Cell Biochem. *73*, 248-258.

Hu, G., Gura, T., Sabsay, B., Sauk, J., Dixit, S.N., and Veis, A. (1995). Endoplasmic reticulum protein Hsp47 binds specifically to the N- terminal globular domain of the amino-propeptide of the procollagen I alpha 1 (I)-chain. Journal of Cellular Biochemistry *59*, 350-367.

Hutchcroft, J.E., Harrison, M.L., and Geahlen, R.L. (1992). Association of the 72-kDa protein-tyrosine kinase PTK72 with the B cell antigen receptor. Journal of Biological Chemistry *267*, 8613-8619.

Kitamura, D., Kudo, A., Schaal, S., Muller, W., Melchers, F., and Rajewsky, K. (1992). A critical role of lambda 5 protein in B cell development. Cell *69*, 823-831.

Kyte, J., and Doolittle, R.F. (1982). A simple method for displaying the hydropathic character of a protein. J. Mol. Biol. 157, 105-132.

Lees, J.F. (1994). The role of cysteine residues in the folding and association of the COOH-terminal propeptide of types I and III procollagen. J.Biol.Chem. 269, 24354-24360.

Lees, J.F. (1997). Identification of the molecular recognition sequence which determines the type-specific assembly of procollagen. EMBO J. 16, 908-916.

Moncur, J.T. (1998). The "Spot 14" gene resides on the telomeric end of the 11q13 amplicon and is expressed in lipogenic breast cancers: implications for control of tumor metabolism. Proc.Natl.Acad.Sci.U.S.A. 95, 6989-6994.

Morino, M., Tsuzuki, T., Iijima, H., Shirakami, T., Kiyosuke, Y.I., Ishikawa, Y., Yoshimura, M., and Yoshikumi, C. (1995). Marked induction of HSP47, a collagen-binding stress protein, during solid tumor formation of ascitic Sarcoma 180 in vivo. In Vivo 9, 503-508.

Morino, M., Tsuzuki, T., Ishikawa, Y., Shirakami, T., Yoshimura, M., Kiyosuke, Matsunaga, K., Yoshikumi, C., and Saijo, N. (1997). Specific expression of HSP47 in human tumor cell lines in vitro. In Vivo 11, 17-21.

Morino, M., Tsuzuki, T., Ishikawa, Y., Shirakami, T., Yoshimura, M., Kiyosuke, Matsunaga, K., Yoshikumi, C., and Saijo, N. (1997). Specific regulation of HSPs in human tumor cell lines by flavonoids. In Vivo 11, 265-270.

Morino, M., Yasuda, T., Shirakami, T., Kiyosuke, Y., Yoshimura, M., Furusho, T., and Yoshikumi, C. (1994). HSP47 as a possible marker for malignancy of tumors in vivo. In Vivo 8, 285-288.

Nagata, K., Saga, S., and Yamada, K.M. (1988). Characterization of a novel transformation-sensitive heat-shock protein (HSP47) that binds to collagen. Biochemical & Biophysical Research Communications 153, 428-434.

Nakai, A., Hirayoshi, K., Saga, S., Yamada, K.M., and Nagata, K. (1989). The transformation-sensitive heat shock protein (hsp47) binds specifically to Fetuin. Biochem.Biophys.Res.Commun. 164, 259-264.

Oliver, J.E. (1996). Mutation in the carboxy-terminal propeptide of the Pro alpha 1(I) chain of type I collagen in a child with severe osteogenesis imperfecta (OI type III): possible implications for protein folding. Hum.Mutat. 7, 318-326.

Pak, B.J., Pang, S.C., and Graham, C.H. (1997). Cellular localization of gp46 at the human fetal-maternal interface. Placenta. *18*, 477-480.

Partidos, C.D., Chirinos-Rojas, C.L., and Steward, M.W. (1997). The potential of combinatorial peptide libraries for the identification of inhibitors of TNF-alpha mediated cytotoxicity in vitro. Immunology Letters 57, 113-116.

Pasqualini, R., Koivunen, E., and Ruoslahti, E. (1996). Peptides in cell adhesion: powerful tools for the study of integrin-ligand interactions. Brazilian Journal of Medical & Biological Research 29, 1151-1158.

Pasqualini, R. and Ruoslahti, E. (1996). Tissue targeting with phage peptide libraries. Molecular Psychiatry *1*, 423

Ruoslahti, E. (1996). RGD and other recognition sequences for integrins. Annual Review of Cell & Developmental Biology *12*, 697-715.

Ruoslahti, E. (1997). Integrins as signaling molecules and targets for tumor therapy. Kidney International *51*, 1413-1417.

Sauk, J.J., Smith, T., Norris, K., and Ferreira, L. (1994). Hsp47 and the translation-translocation machinery cooperate in the production of alpha 1(I) chains of type I procollagen. Journal of Biological Chemistry *269*, 3941-3946.

Sauk, J., Norris, K., Hebert, C., Ordonez, J., and Reynolds, M. (1998). Hsp47 binds to the KDEL receptor and cell surface expression is modulated by cytoplasmic and endosomal pH. Connect.Tissue Res. 37:105-119.

Schuuring, E., Verhoeven, E.M.W.J., and and Michaelides, R.J. (1992). Identification and cloning of two overexpressed genes, U21B31/PRAD1 and EMS1, within the amplified chromosome 11q13 region in human carcinomas. Oncogene. *7*, 355-361.

Shirakami, T., Tsuzuki, T., Iijima, H., Ishikawa, Y., Kiyosuke, Y.I., Morino, M., Yoshimura, M., and Yoshikumi, C. (1995b). Inhibition of HSP47 during the transition from solid to ascitic form of Sarcoma 180 in vivo. In Vivo *9*, 509-512.

Shirakami, T., Tsuzuki, T., Iijima, H., Ishikawa, Y., Kiyosuke, Y.I., Morino, M., Yoshimura, M., and Yoshikumi, C. (1995). Inhibition of HSP47 during the transition from solid to ascitic form of Sarcoma 180 in vivo. In Vivo *9*, 509-512.

Shirakami, T., Tsuzuki, T., Morino, M., Kiyosuke, Y.I., Yoshimura, M., Yoshikumi, C, Okada, F., and Hosokawa, M. (1995a). Decreased expression of HSP47 in highly malignant mouse fibrosarcoma. In Vivo *9*, 513-518.

Smith, G.P. and Scott, J.K. (1993). Libraries of peptides and proteins displayed on filamentous phage. Methods Enzymol. *217:228-57*, 228-257.

Smith, T., Ferreira, L.R., Hebert, C., Norris, K., and Sauk, J.J. (1995). Hsp47 and cyclophilin B traverse the endoplasmic reticulum with procollagen into pre-Golgi intermediate vesicles. A role for Hsp47 and cyclophilin B in the export of procollagen from the endoplasmic reticulum. Journal of Biological Chemistry *270*, 18323-18328.

Takeshita, A., Shinjo, K., Ohnishi, K., and Ohno, R. (1995). New flow cytometric method for detection of minimally expressed multidrug resistance P-glycoprotein on normal and acute leukemia cells using biotinylated MRK16 and streptavidin-RED670 conjugate. Japanese Journal of Cancer Research *86*, 607-615.

Tamura Y, P.P.L.K.D.M.S.P. (1997). Immunotherapy of tumors with autologous tumor-derived heat shock protein preparations. Science *278*, 117-120.

Tang, B.L., Wong, S.H., Low, S.H., Subramaniam, V.N., and Hong, W. (1994). Cytosolic factors block antibody binding to the C-terminal cytoplasmic tail of the KDEL receptor. European Journal of Cell Biology *65*, 298-304.

Tang, B.L., Wong, S.H., Qi, X.L., Low, S.H., and Hong, W. (1993). Molecular cloning, characterization, subcellular localization and dynamics of p23, the mammalian KDEL receptor. Journal of Cell Biology *120*, 325-328.

Weber TM, Joost HG, Simpson IA, and Cushman SW (1988). Subcelluar distribution of Insulin Receptors. In Insulin Receptors. Kahn CR and Harison LC, eds. (New York: Alan R. Liss, Inc), pp. 171-187.

FIGURE LEGENDS

Figure 1. Distribution of Hydophobicity Scores Computed for Peptides Displayed by Bacteriophages Selected from the PhD-7 Library Following Panning Against Hsp47.

The distribution of overall hydrophobicity scores calculated for each peptide using the hydropathy scale of Kyte and Doolittle (1982) are shown for 54 peptides displayed by bacteriophages obtained from Hsp47 binding following three rounds of panning.

Figure 2. Relative Abundance of the 20 Amino Acids In Septapeptides Displayed by the Library of PhD-7 Bacteriophages.

Single stranded DNA was purified from 70 bacteriophage clones from the PhD library, and the sequences of the septapeptides displayed by these bacteriophages were deduced from the DNA sequence of the corresponding region of the bacteriophage genome. The figure shows the frequency of occurrence of each amino acid calculated as the number observed divided by the total number of residues in the 70 septapeptides. The amino acids are grouped according to the number of codons that specify them, and the frequency expected for each group if all codons were utilized with equal efficiency is shown by open bars (Cwirla et al., 1990) . (B) The overall amino acid composition of 54 septapeptides from the Hsp47-binding PhD-7 bacteriophages was compared with that of 70 septapeptides from clones picked randomly from the PhD-7 starting library. The fold increases or fold decrease in the abundance is shown.

Figure 3: Schematic Model of the Peptide-Binding Site of Hsp47.

The peptide backbone is shown as an extended chain. The side chains of two adjacent residues extend into deep pockets in the peptide-binding site that have overall preferences for large hydrophobic or aromatic side chains. The data in figure 3 indicate that amino acids at position 2&3 in septa peptides and 2&3 and/or 11&12 make favorable contacts with Hsp47 side chains. The hydrophobic pockets are flanked by regions that containing charged residues at position 4,5,6 in septapeptides and positions 4 &5 and 7,8,9 & 10 in dodecapeptides.

Figure 4: The Hydropathic Profile of Procollagen I Compared with Selected

Peptides from PhD-12 Library.

Using the Kyte Doolittle method of calculating hydrophilicity (1982) over a window length of 7, selected phage from the PhD-12 library were compared with procollagen I alpha chains. The resides indicated in the boxes above the procollagen I profile indicate the residues similar to Hsp47 binding peptides selected from the PhD-12 library after three rounds of panning. Arrows at the C-propeptide regions indicate amino acids critical for the association and assembly of procollagen (Chessler, 1993b; Lees, 1997; Oliver, 1996; Lees, 1994; Chessler, 1993a).

Figure 5: FITC-antiphage M13 Staining of GMSM-K (Control) and SCC-4 Cells.

Panel a and b represent control GMSM-K cells and SCC-4 cells respectively depicting membrane staining. Panels c and d represent GMSM-K cells and SCC-4 cells respectively, in which the cells have been permeabilized to demonstrate intracellular staining. The areas within the boxes represent FITC staining for phage-peptide.

Figure 6: Immunoprecipitation of Membrane Proteins by Anti-Phage M13 Antibodies.

Bands represent anti-M13 phage binding proteins immunoprecipitated as described in *Methods*. Lanes a-f represent M13 clones selected from PhD-7 and Ph-D12 libraries. Lanes a-c depict PhD-7 clone 3,5,&7 respectively and lanes d-f depict PhD-12 clone 2,5,&9 respectively.

Figure 7: Confocal Microscopic Images of SCC-4 cells Stained with Anti-Hsp47 and Anti-M13 antibodies.

Panel a depicts tumor cell stained with FITC conjugated anti-M13 antibodies, panel b depicts Texas red conjugated anti-Hsp47 antibodies, and panel c depicts spatial co-localization, yellow hues, of FITC and Texas red staining.

Figure 8: Confocal Microscopic Images of SCC-4 cells Stained with FITC-Dextran and Texas red-Anti-M13 antibodies.

Panel a depicts tumor cell stained with FITC conjugated Dextran, panel b depicts Texas red conjugated anti-M13 antibodies, and panel c depicts spatial co-localization of FITC and Texas red staining. Only a minor portion of anti-M13 antibodies co-localizes with FITC-Dextran, yellow hues.

Figure 9:Confocal Microscopic Images of SCC-4 cells Stained with FITC-Transferrin and Texas red-Anti-M13 antibodies.

Panel a depicts tumor cell stained with FITC conjugated Transferrin, panel b depicts Texas red conjugated anti-M13 antibodies, and panel c depicts spatial co-localization, yellow hues, of FITC and Texas red staining.

Figure 10: Fluorescein isothiocyanate Conjugated Dodecapeptide Uptake in SCC Cells. Dodecapeptide corresponding to a cloned peptide was synthesized and conjugated to fluorescein isothiocyanate as described in *Methods*. The peptide was then incubated with SCC-4 cells for 30 min., washed and processed for fluorescence microscopy. The green fluorescence depicted about the nuclear area and in punctate staining represent cellular distribution of the peptide uptake.

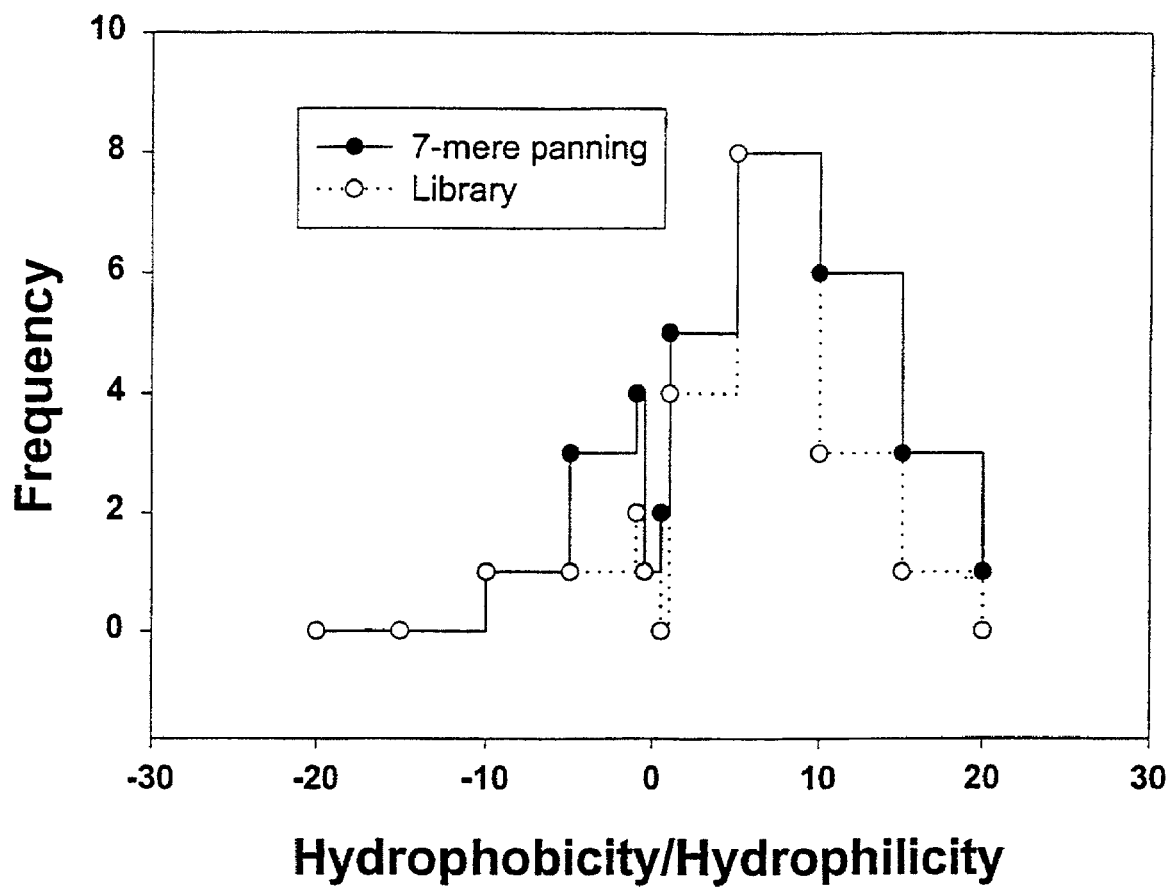

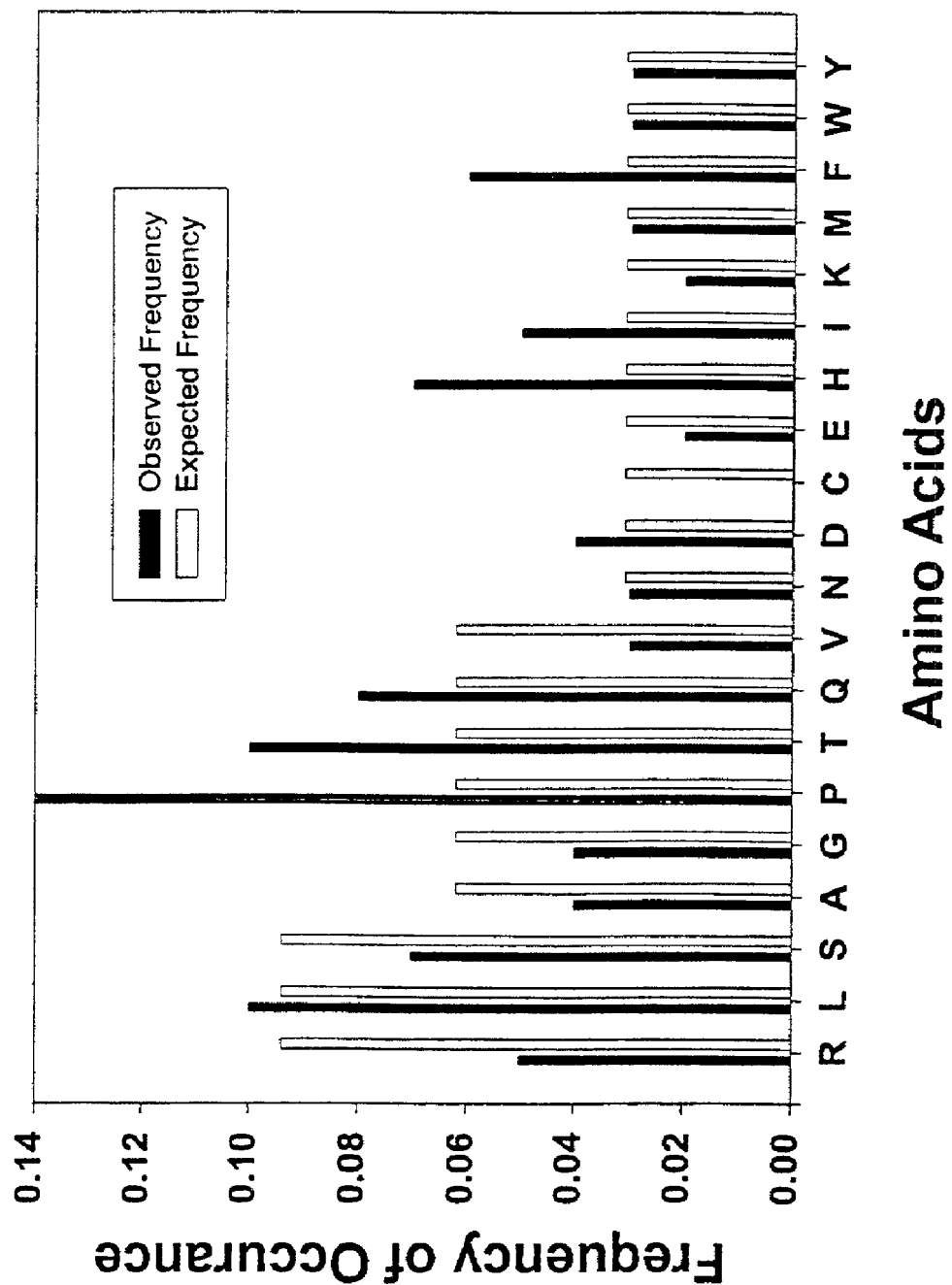

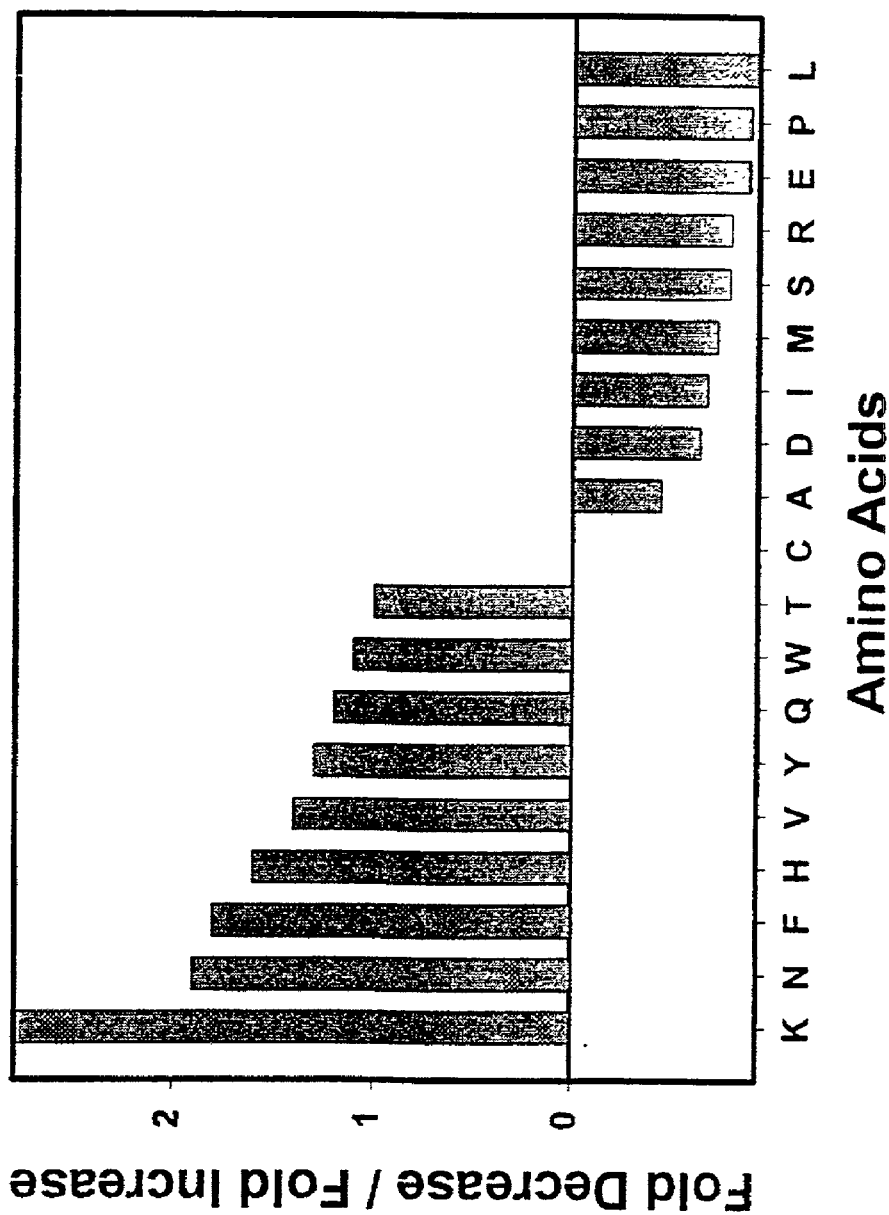

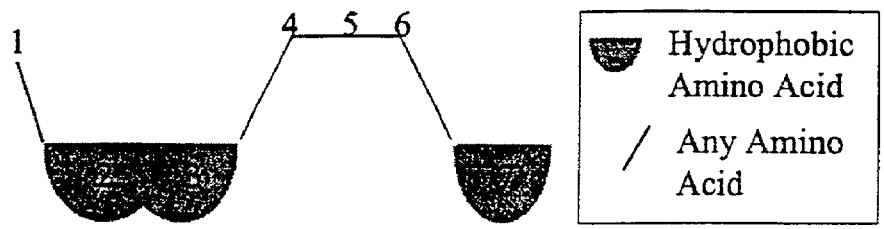
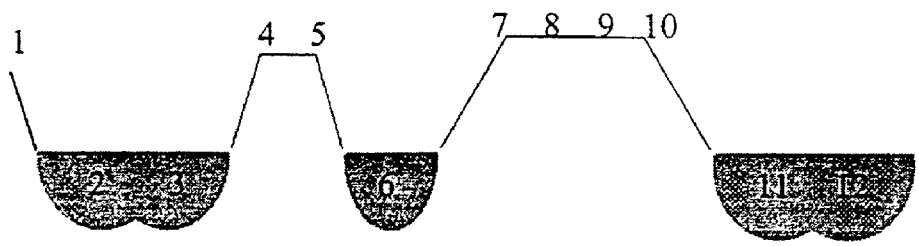

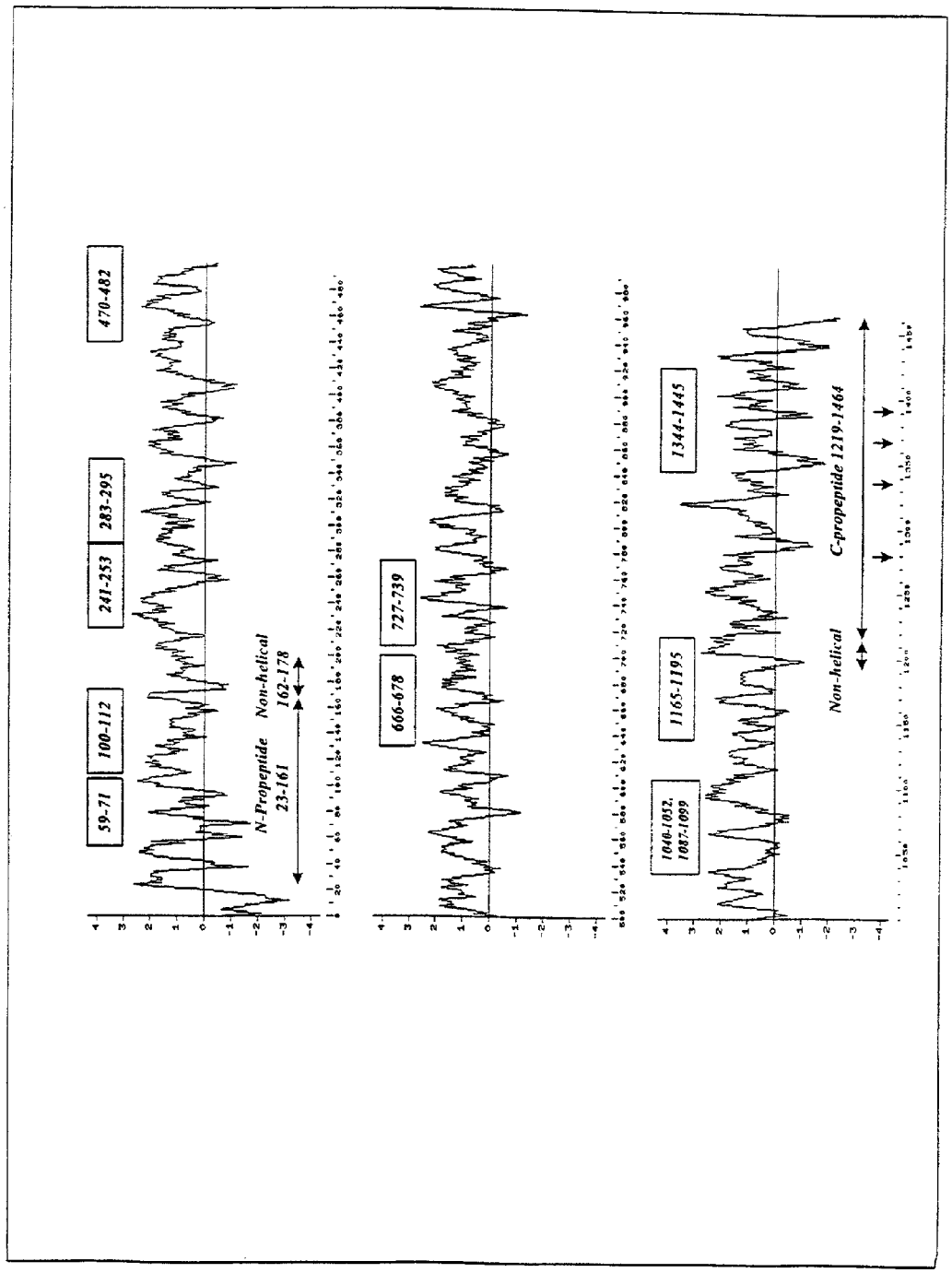

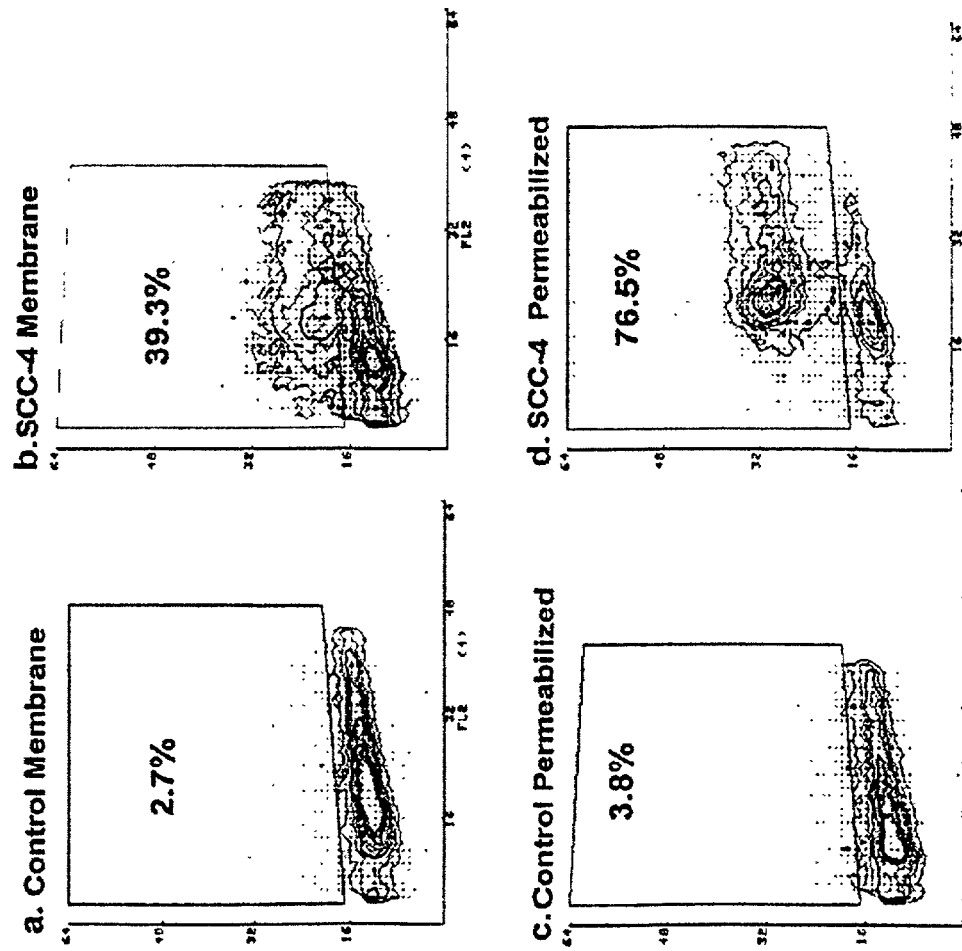

What is claimed is:

1. An isolated peptide which is:
   a) NWTLPTAQFAYL (SEQ. ID NO. 9) or
   b) KVPPALPSPWTS (SEQ. ID NO. 13).

2. A pharmaceutical composition comprising a peptide of claim 1 and a pharmaceutically acceptable carrier.

3. An agent comprising a targeting moiety which binds specifically to an external domain of Hsp47 expressed on the surface of a cell, in an amount effective to modulate the activity of the cell, wherein said targeting moiety comprises the peptide of claim 1.

4. The agent of claim 3, further comprising a therapeutic moiety which is a toxin, a radioisotope or radionuclide, an antibody, or a nucleic acid which encodes a therapeutic gene.

5. The agent of claim 3, wherein said agent further comprising a detectable label which is detectable by MRI, X-Ray, gamma scintigraphy, or CT scanning.

6. A method for treating a patient suffering from a carcinoma in which Hsp47 is expressed on the surface of at least some of cells, comprising administering to the patient an effective amount of an agent comprising a targeting moiety which binds specifically to an external domain of Hsp47, wherein said targeting moiety comprises a peptide of claim 1.

7. The method of claim 6, wherein said targeting moiety further comprises a bacteriophage, wherein said peptide, which binds specifically to an external domain of Hsp47, is on the surface of said bacteriophage.

8. The method of claim 6, wherein the agent further comprises a therapeutic moiety which is a toxin, a radioisotope or radionuclide, an antibody, or a nucleic acid which encodes a therapeutic gene.

9. A method for modulating the interaction of a tumor cell with an intracellular matrix, tumor cell invasion, migration or motility of malignant cells, or tumor cell metastasis comprising contacting said tumor or malignant cell with a peptide of claim 1.

10. A method for modulating a cell which expresses Hsp47 on its surface, comprising administering to the cell an effective amount of an agent comprising a targeting moiety which binds to an external domain of Hsp47, wherein said targeting moiety comprises a peptide of claim 1.

11. The method of claim 6, wherein the Hsp47 is human.

12. A method for detecting a carcinoma in which Hsp47 is expressed on the surface of at least some cells, comprising contacting the carcinoma with a detectable agent comprising a targeting moiety which binds specifically to an external domain of Hsp47, wherein said targeting moiety comprises a peptide of claim 1.

13. The method of claim 12, wherein the detectable agent comprises a detectable moiety which is detectable by MRI, X-Ray, gamma scintigraphy, or CT scanning.

14. A method for detecting a cell which expresses Hsp47 on it surface, comprising administering to the cell a detectable agent comprising a targeting moiety which binds specifically to an external domain of Hsp47, wherein said targeting moiety comprises a peptide of claim 1.

15. The method of claim 12, wherein the Hsp47 is human.

* * * * *

UNITED STATES PATENT AND TRADEMARK OFFICE
CERTIFICATE OF CORRECTION

| | | |
|---|---|---|
| PATENT NO. | : 7,361,730 B1 | Page 1 of 1 |
| APPLICATION NO. | : 09/936565 | |
| DATED | : April 22, 2008 | |
| INVENTOR(S) | : John J. Sauk | |

It is certified that error appears in the above-identified patent and that said Letters Patent is hereby corrected as shown below:

Insert at Column 1, line 8 the heading --STATEMENT REGARDING FEDERALLY SPONSORED RESEARCH OR DEVELOPMENT--

Insert at Column 1, following the above heading --This invention was made with government support under NIH Grant No. DE012606 awarded by the National Institutes of Health. The government has certain rights in the invention.--

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

PATENT NO.        : 7,361,730 B1                                    Page 1 of 1
APPLICATION NO.   : 09/936565
DATED             : April 22, 2008
INVENTOR(S)       : John J. Sauk It is certified that error appears in the above-identified patent and that said Letters Patent is hereby corrected as shown below:

Column 1, line 4 insert -- This invention was made with government support under DE08648 awarded by the National Institutes of Health. The government has certain rights in the invention --

Signed and Sealed this

Twenty-sixth Day of August, 2008

JON W. DUDAS
*Director of the United States Patent and Trademark Office*

SEQUENCE LISTING

<160> NUMBER OF SEQ ID NOS: 68

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Consensus
      motif
<220> FEATURE:
<221> NAME/KEY: MOD_RES
<222> LOCATION: (1)
<223> OTHER INFORMATION: Any amino acid
<220> FEATURE:
<221> NAME/KEY: MOD_RES
<222> LOCATION: (2)..(3)
<223> OTHER INFORMATION: Hydrophobic amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (6)
<223> OTHER INFORMATION: Hydrophobic amino acid
<220> FEATURE:
<221> NAME/KEY: MOD_RES
<222> LOCATION: (7)..(10)
<223> OTHER INFORMATION: Any amino acid
<220> FEATURE:
<221> NAME/KEY: MOD_RES
<222> LOCATION: (11)..(12)
<223> OTHER INFORMATION: Hydrophobic amino acid

<400> SEQUENCE: 1

Xaa Xaa Xaa Xaa Xaa Xaa Xaa Xaa Xaa Xaa Xaa Xaa
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Consensus
      motif
<220> FEATURE:
<221> NAME/KEY: MOD_RES
<222> LOCATION: (1)
<223> OTHER INFORMATION: Hydrophobic amino acid
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (5)..(6)
<223> OTHER INFORMATION: Hydrophobic amino acid
<220> FEATURE:
<221> NAME/KEY: MOD_RES
<222> LOCATION: (7)..(8)
<223> OTHER INFORMATION: Any amino acid
<220> FEATURE:
<221> NAME/KEY: MOD_RES
<222> LOCATION: (9)
<223> OTHER INFORMATION: Hydrophobic amino acid
<220> FEATURE:
<221> NAME/KEY: MOD_RES
<222> LOCATION: (10)..(12)
<223> OTHER INFORMATION: Any amino acid

<400> SEQUENCE: 2

Xaa Xaa Xaa Xaa Xaa Xaa Xaa Xaa Xaa Xaa Xaa Xaa
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp His Trp Gln Trp Thr Pro Trp Ser Ile Gln Pro
  1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp His Tyr Pro Trp Phe Gln Asn Trp Ala Met Ala
  1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp His Trp Asn Gly Trp Lys Tyr Pro Val Val Asp
  1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe His Trp Pro Thr Leu Tyr Asn Met Tyr Ile Pro
  1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Phe His Trp Ser Trp Tyr Thr Pro Ser Arg Pro Ser
  1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 8

Trp His Trp Ser Tyr Pro Leu Trp Gly Pro Leu Glu
  1               5                  10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Trp Thr Leu Pro Thr Ala Gln Phe Ala Tyr Leu
  1               5                  10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Leu Ile Pro Val Lys Ala Leu Arg Ala Val Trp
  1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Pro Gln Pro Asn Met Met Leu Arg Ile Ser Pro
  1               5                  10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Asn Phe Thr Phe Phe Lys Leu Met Pro Val Ser
  1               5                  10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Val Pro Pro Ala Leu Pro Ser Pro Trp Thr Ser
  1               5                  10

<210> SEQ ID NO 14
<211> LENGTH: 12
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Leu Tyr Met His Pro Pro Thr His Thr Met Arg
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Gly Arg Ser Thr Leu Thr Ser Leu Thr Ile Ile
 1               5                  10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Gly Ala Ala Asn Gln Pro Ser Ala Thr Ser Gly
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys His Asn Glu Gln Thr Phe His Pro Lys Val Pro
 1               5                  10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Val Leu His Ser Leu Ala His Gln Thr Phe Ile
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Gln Ser Met Asp Val Tyr Ser Arg Gln Pro Phe
```

-continued

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Thr Pro Thr Ala Pro Trp His Pro Gly Glu Ser
 1               5                  10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Tyr Met Asn Asp His Lys Ser Pro Thr Asp Ser
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Asn Ala Gln Glu Asp Val His Asp Leu Ser Ser
 1               5                  10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Pro Ser Pro Asn Lys Ser Thr Val Ser Pro Gly
 1               5                  10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Phe Met Gln Ala Gln Ala Gly Met Thr His Asn
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 25

Leu Asp Ser Arg Tyr Ser Leu Gln Ala Ala Met Tyr
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Ile Thr Ser Leu Leu Ser
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe His Ser Gly Trp Pro Gln
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Thr Asn Tyr Tyr Thr Asn
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Pro Ala His Arg Ser Tyr
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Asn Ala Ala Thr Glu Tyr
1               5

<210> SEQ ID NO 31

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Leu Ser Met Thr Ile Pro
  1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Val Asn Met Pro Thr Pro
  1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Pro Asn Pro Trp Tyr Gly
  1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Leu Ser Thr Thr Gln Lys
  1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Asp Thr Pro Arg Arg Gln
  1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36
```

```
Lys Leu Thr Asn Thr Val Leu
 1               5
```

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Lys Leu Thr Asn Thr Val Leu
 1               5
```

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Thr Ala Thr Ser Leu Gln Trp
 1               5
```

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Lys Leu Pro Asn Val Asn Ser
 1               5
```

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Asn Val Pro Tyr Val Val His
 1               5
```

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Asp Arg Phe Ser Pro Met Pro
 1               5
```

<210> SEQ ID NO 42
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 42

His Phe Gln Pro Arg His His
 1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

His Ser Thr Ser Thr Pro His
 1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Val Ala Ser Pro Trp Gln
 1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Phe Arg Tyr Asp Thr Phe Pro
 1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

His Asn Tyr Leu Asn Leu Thr
 1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Ser Gln Gly Thr Thr Pro
 1               5
```

-continued

```
<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Glu Phe Leu Pro Val Gln Leu
 1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

His Asn Tyr Leu Asn Leu Thr
 1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

His Pro Ser Leu Asn Lys Pro
 1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His Ser Thr Ser Val Thr Gln
 1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Tyr Val Ala Ser Trp Pro Gln
 1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53
```

```
Ile Thr Val Gln Lys Asn Thr
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Ala Gly Asn Pro Leu Gln
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Phe Thr Ile Pro Ser Asn Leu
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Val Met Ile Lys Gly Gln
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Lys Pro Pro Pro Tyr Asp
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asn Val Pro Tyr Gly Val His
1               5

<210> SEQ ID NO 59
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 59

Ala Phe Leu Pro Ser Lys Leu
 1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

His Phe Gln Pro Arg His His
 1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn Thr Ser Pro Leu Glu Leu
 1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Phe Asn Tyr Asn Pro Leu
 1               5

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 63
ccctcatagt tagcgtaacg                                              20

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Consensus
      motif
<220> FEATURE:
<221> NAME/KEY: MOD_RES
<222> LOCATION: (1)
<223> OTHER INFORMATION: Any amino acid
<220> FEATURE:
<221> NAME/KEY: MOD_RES
<222> LOCATION: (2)..(3)
```

```
<223> OTHER INFORMATION: Hydrophobic amino acid
<220> FEATURE:
<221> NAME/KEY: MOD_RES
<222> LOCATION: (4)..(6)
<223> OTHER INFORMATION: Any amino acid
<220> FEATURE:
<221> NAME/KEY: MOD_RES
<222> LOCATION: (7)..(8)
<223> OTHER INFORMATION: Hydrophobic amino acid

<400> SEQUENCE: 64

Xaa Xaa Xaa Xaa Xaa Xaa Xaa Xaa
  1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Consensus
      motif
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (3)..(4)
<223> OTHER INFORMATION: Hydrophobic amino acid
<220> FEATURE:
<221> NAME/KEY: MOD_RES
<222> LOCATION: (5)..(7)
<223> OTHER INFORMATION: Any amino acid

<400> SEQUENCE: 65

Xaa Xaa Xaa Xaa Xaa Xaa Xaa
  1               5

<210> SEQ ID NO 66
<211> LENGTH: 4
<212> TYPE: PRT
<213> ORGANISM: Unknown Sequence
<220> FEATURE:
<223> OTHER INFORMATION: Description of Unknown Sequence: KDEL receptor

<400> SEQUENCE: 66

Lys Asp Glu Leu
  1

<210> SEQ ID NO 67
<211> LENGTH: 4
<212> TYPE: PRT
<213> ORGANISM: Unknown Sequence
<220> FEATURE:
<223> OTHER INFORMATION: Description of Unknown Sequence: COOH-terminus
      sequence of Hsp47

<400> SEQUENCE: 67

Arg Asp Glu Leu
  1

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Consensus
      motif
<220> FEATURE:
<221> NAME/KEY: MOD_RES
<222> LOCATION: (1)..(5)
```

```
-continued
<223> OTHER INFORMATION: Any amino acid
<220> FEATURE:
<221> NAME/KEY: MOD_RES
<222> LOCATION: (6)
<223> OTHER INFORMATION: Hydrophobic amino acid
<220> FEATURE:
<221> NAME/KEY: MOD_RES
<222> LOCATION: (7)..(8)
<223> OTHER INFORMATION: Any amino acid
<220> FEATURE:
<221> NAME/KEY: MOD_RES
<222> LOCATION: (9)
<223> OTHER INFORMATION: Hydrophobic amino acid
<220> FEATURE:
<221> NAME/KEY: MOD_RES
<222> LOCATION: (10)
<223> OTHER INFORMATION: Any amino acid
<220> FEATURE:
<221> NAME/KEY: MOD_RES
<222> LOCATION: (11)..(12)
<223> OTHER INFORMATION: Hydrophobic amino acid

<400> SEQUENCE: 68

Xaa Xaa Xaa Xaa Xaa Xaa Xaa Xaa Xaa Xaa Xaa Xaa
 1               5                  10
```